(12) United States Patent
Ohsawa et al.

(10) Patent No.: US 7,101,651 B2
(45) Date of Patent: *Sep. 5, 2006

(54) SULFONYLDIAZOMETHANES, PHOTOACID GENERATORS, RESIST COMPOSITIONS, AND PATTERNING PROCESS

(75) Inventors: Youichi Ohsawa, Niigata-ken (JP); Katsuhiro Kobayashi, Niigata-ken (JP); Yoshitaka Yanagi, Niigata-ken (JP); Kazunori Maeda, Niigata-ken (JP)

(73) Assignee: Shin-Etsu Chemical Co.,Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/776,291

(22) Filed: Feb. 12, 2004

(65) Prior Publication Data
US 2004/0166432 A1    Aug. 26, 2004

(30) Foreign Application Priority Data
Feb. 13, 2003    (JP)    ............................ 2003-035055

(51) Int. Cl.
*G03F 7/004*    (2006.01)
*G03F 7/30*    (2006.01)

(52) U.S. Cl. .................. 430/170; 430/270.1; 430/326; 430/905; 534/558

(58) Field of Classification Search .............. 430/170, 430/270.1, 905, 326; 534/558
See application file for complete search history.

(56) References Cited

U.S. PATENT DOCUMENTS

| | | | |
|---|---|---|---|
| 2,354,229 A | | 7/1944 | Walter .................. 260/609 |
| 5,338,641 A | * | 8/1994 | Pawlowski et al. .......... 430/165 |
| 5,424,166 A | * | 6/1995 | Pawlowski et al. .......... 430/157 |
| 5,558,971 A | * | 9/1996 | Urano et al. ................. 430/170 |
| 5,558,976 A | * | 9/1996 | Urano et al. ................. 430/326 |
| 5,945,517 A | * | 8/1999 | Nitta et al. .................. 534/558 |
| 6,004,724 A | | 12/1999 | Yamato et al. ........... 430/281.1 |
| 6,136,502 A | | 10/2000 | Satoshi et al. ............ 430/270.1 |
| 6,261,738 B1 | | 7/2001 | Asakura et al. .......... 430/270.1 |
| 6,395,446 B1 | * | 5/2002 | Seki et al. .................. 430/170 |
| 6,689,530 B1 | * | 2/2004 | Ohsawa et al. ............. 430/170 |
| 2003/0180653 A1 | * | 9/2003 | Ohsawa et al. ............. 430/170 |
| 2004/0167322 A1 | * | 8/2004 | Ohsawa et al. ............. 534/882 |

FOREIGN PATENT DOCUMENTS

| | | |
|---|---|---|
| JP | 3-103854 A | 4/1991 |
| JP | 4-211258 A | 8/1992 |
| JP | 6-266112 A | 9/1994 |
| JP | 8-123032 A | 5/1996 |
| JP | 9-95479 A | 4/1997 |
| JP | 9-208554 A | 8/1997 |
| JP | 9-230588 A | 9/1997 |
| JP | 9-301948 A | 11/1997 |
| JP | 10-90884 A | 4/1998 |
| JP | 11-38604 A | 2/1999 |
| JP | 11-72921 A | 3/1999 |
| JP | 2906999 B2 | 4/1999 |
| JP | 11-190904 A | 7/1999 |
| JP | 2000-314956 A | 11/2000 |
| JP | 2000-344836 A | 12/2000 |
| JP | 2001-55373 A | 2/2001 |
| JP | 2001-106669 A | 4/2001 |

OTHER PUBLICATIONS

Paquette et al., J. Am. Chem. Soc., vol. 86, pp. 4383-4385, (1964).
Walter et al., J. Am. Chem. Soc., vol. 67, pp. 655-657, (1945).
Wagner et al., Synthetic Organic Chemistry, pp. 778-781, (1965).
Arimitsu et al., J. Photopolymer Science & Tech., vol. 9, No. 1, pp. 29-30, (1996).
Arimitsu et al., J. Photopolymer Science & Tech., vol. 8, No. 1, pp. 43-44, (1995).
Kudo et al., J. Photopolymer Science & Tech., vol. 8, No. 1, pp. 45-46, (1995).

* cited by examiner

*Primary Examiner*—John S. Chu
(74) *Attorney, Agent, or Firm*—Birch, Stewart, Kolasch & Birch, LLP

(57) ABSTRACT

A chemical amplification type resist composition comprising a specific sulfonyldiazomethane containing long-chain alkoxyl groups has many advantages including improved resolution, improved focus latitude, minimized line width variation or shape degradation even on long-term PED, minimized debris left after coating, development and peeling, and improved pattern profile after development and is thus suited for microfabrication.

15 Claims, No Drawings

SULFONYLDIAZOMETHANES, PHOTOACID GENERATORS, RESIST COMPOSITIONS, AND PATTERNING PROCESS

This Nonprovisional application claims priority under 35 U.S.C. § 119(a) on Patent Application No(s). 2003-035055 filed in Japan on Feb. 13, 2003, the entire contents of which are hereby incorporated by reference.

This invention relates to novel sulfonyldiazomethane compounds, photoacid generators for resist compositions, resist compositions comprising the photoacid generators, and a patterning process using the same. The resist compositions, especially chemical amplification type resist compositions are sensitive to such radiation as UV, deep UV, electron beams, x-rays, excimer laser beams, γ-rays, and synchrotron radiation and suitable for the microfabrication of integrated circuits.

BACKGROUND OF THE INVENTION

While a number of efforts are currently being made to achieve a finer pattern rule in the drive for higher integration and operating speeds in LSI devices, deep-ultraviolet lithography is thought to hold particular promise as the next generation in microfabrication technology.

One technology that has attracted a good deal of attention recently utilizes as the deep UV light source a high-intensity KrF excimer laser, especially an ArF excimer laser featuring a shorter wavelength. There is a desire to have a microfabrication technique of finer definition by combining exposure light of shorter wavelength with a resist material having a higher resolution.

In this regard, the recently developed, acid-catalyzed, chemical amplification type resist materials are expected to comply with the deep UV lithography because of their many advantages including high sensitivity, resolution and dry etching resistance. The chemical amplification type resist materials include positive working materials that leave the unexposed areas with the exposed areas removed and negative working materials that leave the exposed areas with the unexposed areas removed.

In chemical amplification type, positive working, resist compositions to be developed with alkaline developers, an alkali-soluble phenol or a resin and/or compound in which carboxylic acid is partially or entirely protected with acid-labile protective groups (acid labile groups) is catalytically decomposed by an acid which is generated upon exposure, to thereby generate the phenol or carboxylic acid in the exposed area which is removed by an alkaline developer. Also, in similar negative working resist compositions, an alkali-soluble phenol or a resin and/or compound having carboxylic acid and a compound (crosslinking agent) capable of bonding or crosslinking the resin or compound under the action of an acid are crosslinked with an acid which is generated upon exposure whereby the exposed area is converted to be insoluble in an alkaline developer and the unexposed area is removed by the alkaline developer.

On use of the chemical amplification type, positive working, resist compositions, a resist film is formed by dissolving a resin having acid labile groups as a binder and a compound capable of generating an acid upon exposure to radiation (to be referred to as photoacid generator) in a solvent, applying the resist solution onto a substrate by a variety of methods, and evaporating off the solvent optionally by heating. The resist film is then exposed to radiation, for example, deep UV through a mask of a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally the remaining resist film is removed by dissolution in a remover solution or ashing, leaving the substrate having the desired pattern profile.

The chemical amplification type, positive working, resist compositions adapted for KrF excimer lasers generally use a phenolic resin, for example, polyhydroxystyrene in which some or all of the hydrogen atoms of phenolic hydroxyl groups are protected with acid labile protective groups. Iodonium salts, sulfonium salts, and bissulfonyldiazomethane compounds are typically used as the photoacid generator. If necessary, there are added additives, for example, a dissolution inhibiting or promoting compound in the form of a carboxylic acid and/or phenol derivative having a molecular weight of up to 3,000 in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

Bissulfonyldiazomethanes as shown below are advantageously used as the photoacid generator in chemical amplification type resist compositions, especially chemical amplification type, positive working, resist compositions adapted for KrF excimer lasers because they provide a high sensitivity and resolution and eliminate poor compatibility with resins and poor solubility in resist solvents as found with the sulfonium and iodonium salt photoacid generators.

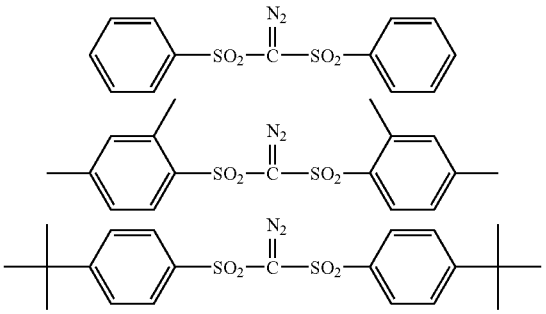

Although these photoacid generators are highly lipophilic and highly soluble in resist solvents, they have poor affinity to or solubility in developers so that upon development and/or resist removal, the photoacid generators can be left on the substrate as insoluble matter (consisting of the photoacid generator or a mixture thereof with the resin).

For example, upon development, the resist material which has poor affinity to or solubility in a developer deposits on developed spaces in the exposed area or on lines in the unexposed area as foreign matter.

JP-A 3-103854 discloses bis(4-methoxyphenylsulfonyl) diazomethane as a photoacid generator having a methoxy group introduced therein. As long as we confirmed, the methoxy group is not fully effective. The photoacid generator is often left on the substrate as insoluble matter (consisting of the photoacid generator or a mixture thereof with the resin) upon development and/or resist film removal.

If unsubstituted bis(phenylsulfonyl)diazomethane or bis (cyclohexylsulfonyl)diazomethane having alkyl groups instead of aryl groups is used in a resist material as the photoacid generator for reducing lipophilic property, resolution is deteriorated. If it is added in large amounts, the problem of insoluble matter upon development and/or resist film removal remains unsolved.

Aside from the countermeasure for foreign matter, JP-A 10-90884 discloses to introduce such an acid labile group as t-butoxycarbonyloxy, ethoxyethyl or tetrahydropyranyl into disulfonediazomethane for the purpose of improving the contrast of positive resist material. We empirically found that these compounds are unstable and ineffective for eliminating the foreign matter upon development and resist film removal.

Searching for a countermeasure to the foreign matter problem, we already synthesized sulfonyldiazomethanes having an acyl group (e.g., acetyl) or methanesulfonyl group introduced therein and found that they were useful as the photoacid generator in chemical amplification type resist composition. Since these arylsulfonyldiazomethanes having an acyl group or methanesulfonyl group introduced therein lack stability under basic conditions during their synthesis, the yield of diazo formation is sometimes low. See JP-A 2001-055373 and JP-A 2001-106669.

It is known from JP-A 8-123032 to use two or more photoacid generators in a resist material. JP-A 11-72921 discloses the use of a radiation-sensitive acid generator comprising in admixture a compound which generates a sulfonic acid having at least three fluorine atoms upon exposure to radiation and a compound which generates a fluorine atom-free sulfonic acid upon exposure to radiation, thereby improving resolution without inviting nano-edge roughness and film surface roughening. JP-A 11-38604 describes that a resist composition comprising an asymmetric bissulfonyldiazomethane such as a bissulfonyldiazomethane having alkylsulfonyl and arylsulfonyl groups or a bissulfonyldiazomethane having arylsulfonyl and alkoxy-substituted arylsulfonyl groups and a polyhydroxystyrene derivative having acid labile groups as the polymer has a resolution at least comparable to prior art compositions, a sufficient sensitivity and significantly improved heat resistance. However, we empirically found that these resist compositions are unsatisfactory in resolution and in the effect of eliminating the foreign matter on the pattern upon development. From the synthetic and industrial standpoints, it is difficult to obtain bilaterally asymmetric bissulfonyl-diazomethanes.

Aside from the above-discussed problem of insoluble matter upon development and/or removal, there is also a problem that the pattern profile often changes when the period from exposure to post-exposure baking (PEB) is prolonged, which is known as post-exposure delay (PED). Such changes frequently reveal as a slimming of the line width of unexposed areas in the case of chemical amplification type positive resist compositions using acetal and analogous acid labile groups, and as a thickening of the line width of unexposed areas in the case of chemical amplification type positive resist compositions using tert-butoxycarbonyl (t-BOC) and analogous acid labile groups. Since the period from exposure to PEB is often prolonged for the operational reason, there is a desire to have a stable resist composition which is free from such changes, that is, has PED stability.

In some resist processes, baking is performed at far higher temperatures (e.g., 130° C.) than the customary baking temperature of 120° C. or below as disclosed in JP-A 6-266112. In this case, the bissulfonyldiazomethanes shown above by structural formulae can be thermally decomposed to generate acids due to their low heat resistance so that acidolysis takes place everywhere regardless of whether the areas are exposed or unexposed, failing in pattern formation.

The solubility of photosensitive agents or photoacid generators was the problem from the age when quinonediazide photosensitive agents were used in non-chemical amplification type resist materials. Specific considerations include the solubility of photoacid generators in resist solvents, the compatibility of photoacid generators with resins, the solubility (or affinity) of photo-decomposed products after exposure and PEB and non-decomposed compound (photoacid generator) in a developer, and the solubility of the photoacid generator and photo-decomposed products thereof in a remover solvent upon resist removal or peeling. If these factors are poor, there can occur problems including precipitation of the photoacid generator during storage, difficulty of filtration, uneven coating, striation, abnormal resist sensitivity, and foreign matter, left-over and staining on the pattern and in spaces after development.

The photoacid generator in resist material is required to meet a fully high solubility in (or compatibility with) a resist solvent and a resin, good storage stability, non-toxicity, effective coating, a well-defined pattern profile, PED stability, and no foreign matter left during pattern formation after development and upon resist removal. The conventional photoacid generators, especially diazodisulfone photoacid generators do not meet all of these requirements.

As the pattern of integrated circuits becomes finer in these days, a higher resolution is, of course, required, and the problem of foreign matter after development and resist removal becomes more serious.

SUMMARY OF THE INVENTION

An object of the invention is to provide a novel sulfonyl-diazomethane for use in a resist composition, especially of the chemical amplification type, such that the resist composition minimizes the foreign matter left after coating, development and resist removal and ensures a well-defined pattern profile after development. Another object of the invention is to provide a photoacid generator for resist compositions, a resist composition comprising the photoacid generator, and a patterning process using the same.

We have found that by using a sulfonyldiazomethane compound of the general formula (1), especially formula (1a), to be defined below, as the photoacid generator in a resist composition, there are achieved a number of advantages including dissolution, storage stability, effective coating, minimized line width variation or shape degradation during long-term PED, minimized foreign matter left after coating, development and resist removal, a well-defined pattern profile after development, and a high resolution enough for microfabrication, especially by deep UV lithography. Better results are obtained when a sulfonyldiazomethane compound of the formula (1), especially formula (1a), is used as the photoacid generator in a chemical amplification type resist composition, typically chemical amplification positive type resist composition comprising a resin which changes its solubility in an alkaline developer under the action of an acid as a result of scission of C—O—C linkages. The composition exerts its effect to the maximum extent when processed by deep UV lithography.

In a first aspect, the invention provides a sulfonyldiazomethane compound having the following general formula (1).

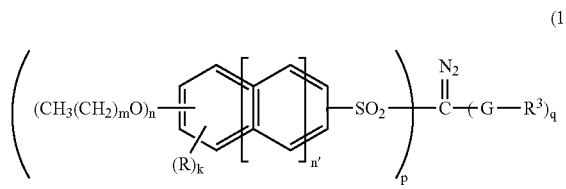

Herein R is independently hydrogen or a substituted or unsubstituted straight, branched or cyclic alkyl or alkoxy group of 1 to 4 carbon atoms, G is $SO_2$ or CO, $R^3$ is a substituted or unsubstituted straight, branched or cyclic alkyl group of 1 to 10 carbon atoms or a substituted or unsubstituted aryl group of 6 to 14 carbon atoms, p is 1 or 2, q is 0 or 1, satisfying p+q=2, n is 2 or 3, n' is 0 or 1, m is independently an integer of 3 to 11, and k is an integer of 0 to 4.

Typical sulfonyldiazomethane compounds have the following general formula (1a).

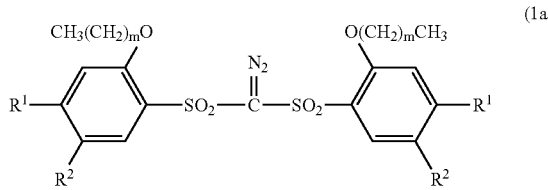

Herein $R^1$ and $R^2$ are each independently R or $CH_3(CH_2)_mO$, excluding the combination that both $R^1$ and $R^2$ are R at the same time, R and m are as defined above.

In a second aspect, the invention provides a photoacid generator for a chemical amplification type resist composition comprising the sulfonyldiazomethane compound of formula (1) or (1a).

In a third aspect, the invention provides a chemical amplification type resist composition comprising (A) a resin which changes its solubility in an alkaline developer under the action of an acid, (B) the sulfonyldiazomethane compound of formula (1) or (1a) which generates an acid upon exposure to radiation, and optionally, (C) a compound capable of generating an acid upon exposure to radiation, other than component (B). The resist composition may further contain (D) a basic compound, (E) an organic acid derivative, and an organic solvent.

The resin (A) typically has such substituent groups having C—O—C linkages that the solubility in an alkaline developer changes as a result of scission of the C—O—C linkages under the action of an acid.

In a preferred embodiment, the resin (A) is a polymer containing phenolic hydroxyl groups in which hydrogen atoms of the phenolic hydroxyl groups are substituted with acid labile groups of one or more types in a proportion of more than 0 mol % to 80 mol % on the average of the entire hydrogen atoms of the phenolic hydroxyl groups, the polymer having a weight average molecular weight of 3,000 to 100,000.

More preferably, the resin (A) is a polymer comprising recurring units of the following general formula (2a):

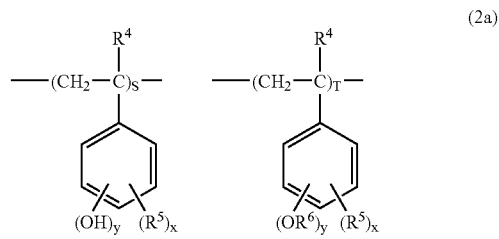

wherein $R^4$ is hydrogen or methyl, $R^5$ is a straight, branched or cyclic alkyl group of 1 to 8 carbon atoms, x is 0 or a positive integer, y is a positive integer, satisfying x+y≦5, $R^6$ is an acid labile group, S and T are positive integers, satisfying 0<T/(S+T)≦0.8, wherein the polymer contains units in which hydrogen atoms of phenolic hydroxyl groups are partially substituted with acid labile groups of one or more types, a proportion of the acid labile group-bearing units is on the average from more than 0 mol % to 80 mol % based on the entire polymer, and the polymer has a weight average molecular weight of 3,000 to 100,000.

In another preferred embodiment, the resin (A) is a polymer comprising recurring units of the following general formula (2a'):

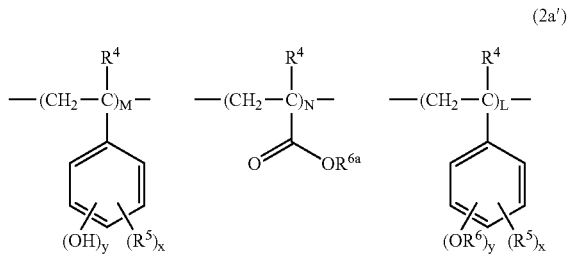

wherein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, at least some of $R^{6a}$ being acid labile groups, x is 0 or a positive integer, y is a positive integer, satisfying x+y≦5, M and N are positive integers, L is 0 or a positive integer, satisfying $0<N/(M+N+L)\leqq 0.5$ and $0<(N+L)/(M+N+L)\leqq 0.8$, wherein the polymer contains on the average from more than 0 mol % to 50 mol % of those units derived from acrylate and methacrylate, and also contains on the average from more than 0 mol % to 80 mol % of acid labile group-bearing units, based on the entire polymer, and the polymer has a weight average molecular weight of 3,000 to 100,000.

In a further preferred embodiment, the resin (A) is a polymer comprising recurring units of the following general formula (2a"):

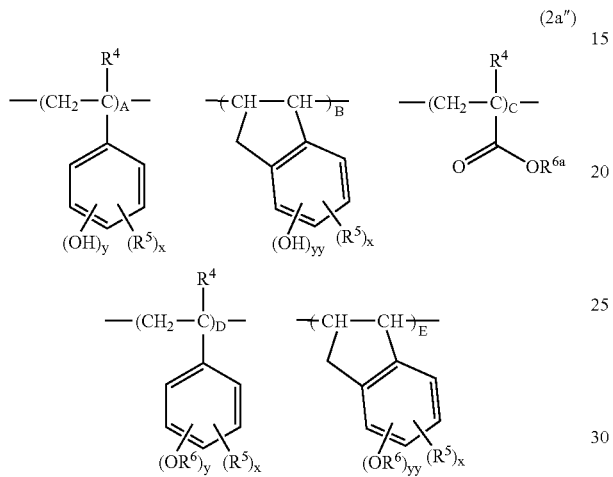

(2a")

wherein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, at least some of $R^{6a}$ being acid labile groups, x is 0 or a positive integer, y is a positive integer, satisfying $x+y\leqq 5$, yy is 0 or a positive integer, satisfying $x+yy\leqq 5$, A and B are positive integers, C, D and E each are 0 or a positive integer, satisfying $0<(B+E)/(A+B+C+D+E)\leqq 0.5$ and $0<(C+D+E)/(A+B+C+D+E)\leqq 0.8$, wherein the polymer contains on the average from more than 0 mol % to 50 mol % of those units derived from indene and/or substituted indene, and also contains on the average from more than 0 mol % to 80 mol % of acid labile group-bearing units, based on the entire polymer, and the polymer has a weight average molecular weight of 3,000 to 100,000.

In these preferred embodiments, the acid labile group is selected from the class consisting of groups of the following general formulae (4) to (7), tertiary alkyl groups of 4 to 20 carbon atoms, trialkylsilyl groups whose alkyl moieties each have 1 to 6 carbon atoms, oxoalkyl groups of 4 to 20 carbon atoms, and aryl-substituted alkyl groups of 7 to 20 carbon atoms.

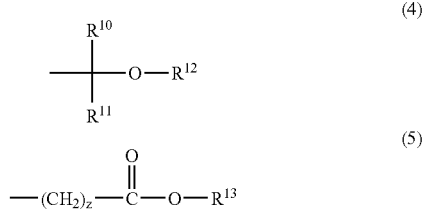

(4)

(5)

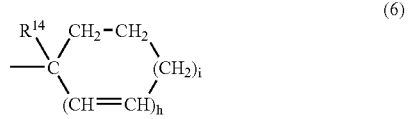

(6)

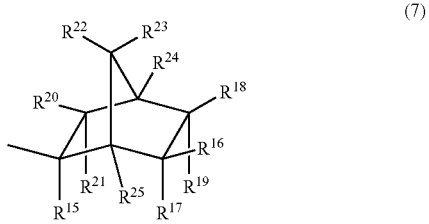

(7)

Herein $R^{10}$ and $R^{11}$ each are hydrogen or a straight, branched or cyclic alkyl having 1 to 18 carbon atoms, and $R^{12}$ is a monovalent hydrocarbon group of 1 to 18 carbon atoms which may contain a heteroatom, a pair of $R^{10}$ and $R^{11}$, $R^{10}$ and $R^{12}$, or $R^{11}$ and $R^{12}$ may together form a ring, with the proviso that $R^{10}$, $R^{11}$, and $R^{12}$ each are a straight or branched alkylene of 1 to 18 carbon atoms when they form a ring, $R^{13}$ is a tertiary alkyl group of 4 to 20 carbon atoms, a trialkysilyl group in which each of the alkyls has 1 to 6 carbon atoms, an oxoalkyl group of 4 to 20 carbon atoms, or a group of the formula (4), z is an integer of 0 to 6, $R^{14}$ is a straight, branched or cyclic alkyl group of 1 to 8 carbon atoms or an aryl group of 6 to 20 carbon atoms which may be substituted, h is 0 or 1, i is 0, 1, 2 or 3, satisfying $2h+i=2$ or 3, $R^{15}$ is a straight, branched or cyclic alkyl group of 1 to 8 carbon atoms or an aryl group of 6 to 20 carbon atoms which may be substituted, $R^{16}$ to $R^{25}$ are each independently hydrogen or a monovalent hydrocarbon group of 1 to 15 carbon atoms which may contain a heteroatom, any two of $R^{16}$ to $R^{25}$, taken together, may form a ring, each of the ring-forming two of $R^{16}$ to $R^{25}$ is a divalent hydrocarbon group of 1 to 15 carbon atoms which may contain a heteroatom, or two of $R^{16}$ to $R^{25}$ which are attached to adjoining carbon atoms may bond together directly to form a double bond.

Preferably, the resist composition contains a propylene glycol alkyl ether acetate, an alkyl lactate or a mixture thereof as the organic solvent.

Also contemplated herein is a process for forming a pattern, comprising the steps of applying the resist composition onto a substrate to form a coating; heat treating the coating and exposing the coating to high energy radiation with a wavelength of up to 300 nm or electron beam through a photomask; optionally heat treating the exposed coating, and developing the coating with a developer.

DESCRIPTION OF THE PREFERRED EMBODIMENTS

Sulfonyldiazomethane

In the first aspect of the invention, novel sulfonyldiazomethane compounds having long-chain alkoxyl groups are provided. They are represented by the general formula (1).

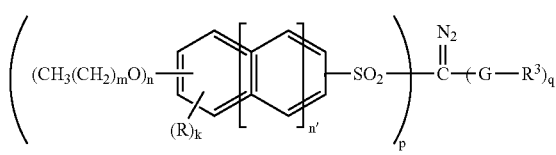

(1)

Herein R is each independently hydrogen or a substituted or unsubstituted straight, branched or cyclic alkyl or alkoxy group of 1 to 4 carbon atoms, G is $SO_2$ or CO, $R^3$ is a substituted or unsubstituted straight, branched or cyclic alkyl group of 1 to 10 carbon atoms or a substituted or unsubstituted aryl group of 6 to 14 carbon atoms, p is 1 or 2, q is 0 or 1, satisfying p+q=2, n is 2 or 3, n' is 0 or 1, m is independently an integer of 3 to 11, and k is an integer of 0 to 4.

Preferred among the sulfonyldiazomethane compounds of formula (1) are sulfonyldiazomethane compounds having long-chain alkoxyl groups of the following general formula (1a).

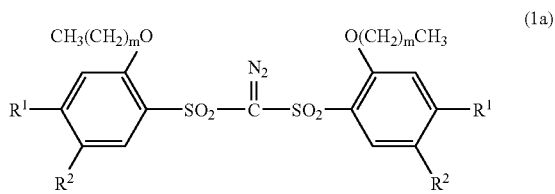

(1a)

Herein $R^1$ and $R^2$ are each independently R or $CH_3(CH_2)_mO$, excluding the combination that both $R^1$ and $R^2$ are R at the same time, wherein R is hydrogen or a substituted or unsubstituted straight, branched or cyclic alkyl or alkoxy group of 1 to 4 carbon atoms, and m is an integer of 3 to 11.

In formulae (1) and (1a), R may be the same or different and stands for hydrogen or substituted or unsubstituted, straight, branched or cyclic alkyl or alkoxy groups of 1 to 4 carbon atoms, for example, hydrogen, methyl, ethyl, n-propyl, sec-propyl, cyclopropyl, n-butyl, sec-butyl, iso-butyl, tert-butyl, methoxy, ethoxy, n-propyloxy, sec-propyloxy, n-butyloxy, sec-butyloxy, iso-butyloxy, and tert-butyloxy. Of these, hydrogen, methyl, ethyl, n-propyl and isopropyl are preferred, with hydrogen and methyl being most preferred.

The subscript k is an integer of 0 to 4, and k is preferably 0, 1 or 2 when R is $C_{1-4}$ alkyl or alkoxy. The substitution position of R is arbitrary. The preferred substitution position of R is the 2-position (ortho position) relative to the sulfonyl group when n' is 0 and no long-chain alkoxyl group is attached at the 2-position (ortho position) relative to the sulfonyl group. It is more preferred that methyl be located at the 2-position (ortho position) relative to the sulfonyl group. When k is 2 to 4, substituent groups (R) which may be either identical or different may be further located at positions other than 2-position.

$R^3$ stands for substituted or unsubstituted, straight, branched or cyclic alkyl groups of 1 to 10 carbon atoms or substituted or unsubstituted aryl groups of 6 to 14 carbon atoms. Illustrative, non-limiting, examples of the straight, branched or cyclic alkyl groups include methyl, ethyl, n-propyl, sec-propyl, n-butyl, sec-butyl, iso-butyl, tert-butyl, n-pentyl, sec-pentyl, cyclopentyl, n-hexyl, and cyclohexyl. Illustrative, non-limiting, examples of the substituted or unsubstituted aryl groups include phenyl, 4-methylphenyl, 4-ethylphenyl, 4-methoxyphenyl, 4-tert-butylphenyl, 4-tert-butoxyphenyl, 4-cyclohexylphenyl, 4-cyclohexyloxyphenyl, 2,4-dimethylphenyl, 2,4,6-trimethylphenyl, 2,4,6-triisopropylphenyl, 1-naphthyl and 2-naphthyl. Of these, tert-butyl, cyclohexyl, 4-methylphenyl, 2,4-dimethylphenyl and 4-tert-butylphenyl are preferred. G stands for $SO_2$ or CO. $SO_2$ is preferred.

It is noted that the substituted alkyl groups include halogenated alkyl groups (e.g., chloro or fluoro-substituted ones), carbonyl-containing alkyl groups, and alkyl groups having a carbonyl group protected with an acetal (ketal). The substituted aryl groups include halogenated aryl groups (e.g., chloro or fluoro-substituted ones) and straight, branched or cyclic alkoxy group-substituted aryl groups. Specific examples include 2,4-difluorophenyl, 4-trifluoromethylphenyl, and groups of the following formulae.

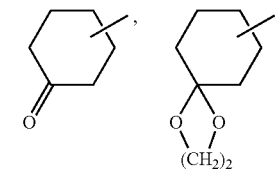

The subscript p is equal to 1 or 2, q is equal to 0 or 1, satisfying p+q=2. The subscript n is equal to 2 or 3. Preference is given to n=2 for ease of availability of starting reactants and ease of synthesis. The subscript n' is 0 or 1. Preference is given to n'=0 for ease of availability of starting reactants and the boiling point of intermediate reactants. The subscript m is an integer of 3 to 11, preferably an integer of 3 to 5 as long as the boiling point of intermediate reactants is concerned.

The sulfonyldiazomethane compounds can be synthesized by the following method although the synthesis method is not limited thereto.

Reference is first made to a sulfonyldiazomethane compound of formula (1) wherein p=2, that is, a symmetric bissulfonyldiazomethane compound. It is desirably synthesized by condensing a substituted thiophenol or thionaphthol with dichloromethane under basic conditions as disclosed in JP-A 3-103854. More specifically, a long chain alkoxyl-containing thiophenol such as 2,4-bis(n-butyloxy)thiophenol is condensed with dichloromethane in an alcohol solvent such as methanol or ethanol in the presence of a base such as sodium hydroxide or potassium hydroxide, obtaining a formaldehyde bis(alkoxyphenylthio)acetal.

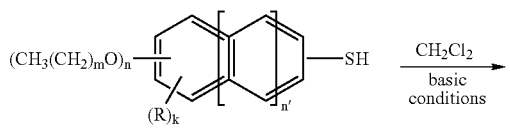

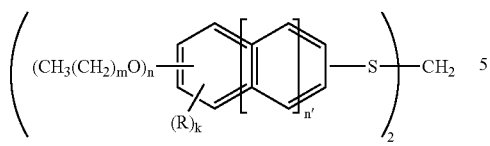

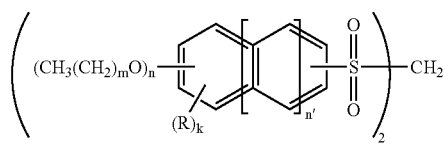

Herein, R, m, n, n' and k are as defined above.

Alternatively, a substituted thiophenol or thionaphthol is condensed with a formaldehyde (typically paraformaldehyde) under acidic conditions such as sulfuric acid or trifluoromethanesulfonic acid.

In the case of p=1, that is, an asymmetric sulfonyldiazomethane compound, reaction is effected between a halomethyl thioether and an alkoxy-substituted thiophenol or thionaphthol. In the case of sulfonylcarbonyldiazomethane, reaction is conducted between an α-halomethylketone and an alkoxy-substituted thiophenol or thionaphthol. The halomethyl thioether can be prepared from a corresponding thiol, formaldehyde and hydrogen chloride (see J. Am. Chem. Soc., 86, 4383 (1964), J. Am. Chem. Soc., 67, 655 (1945), and U.S. Pat. No. 2,354,229).

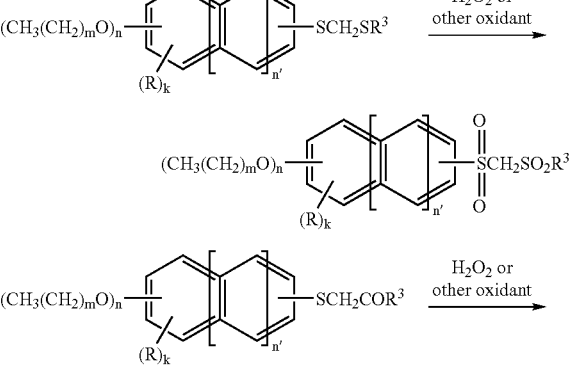

Herein, R, $R^3$, m, n, n' and k are as defined above.

This product is reacted with p-toluenesulfonylazide, p-dodecylbenzenesulfonylazide or p-acetamidobenzenesulfonylazide under basic conditions into a diazo form, yielding the end sulfonyldiazomethane.

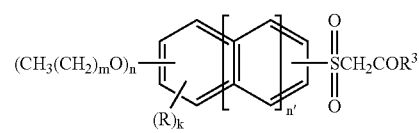

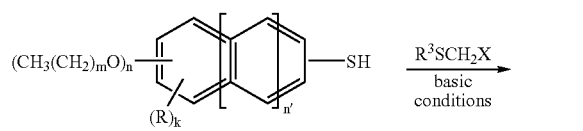

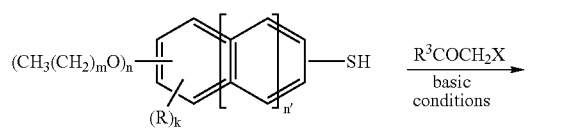

Herein, R, $R^3$, m, n, n' and k are as defined above, and X is a halogen atom.

Further, the product is oxidized with an oxidant such as aqueous hydrogen peroxide in the presence of sodium tungstate etc. as described in JP-A 4-211258, yielding a corresponding sulfonylmethane.

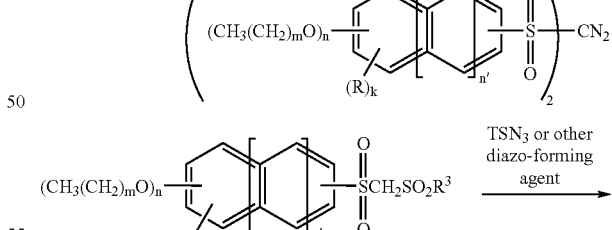

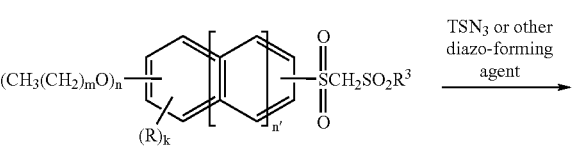

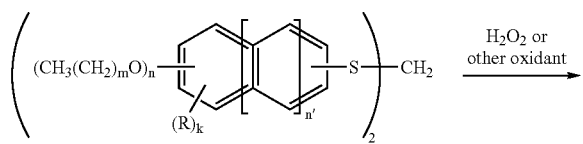

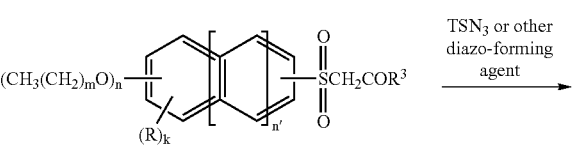

-continued

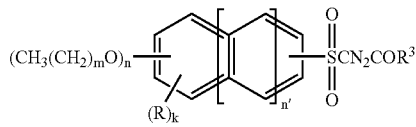

Herein, R, R³, m, n, n' and k are as defined above.

It is noted that the synthesis of alkoxy-substituted thiophenols or thionaphthols is not critical. They can be synthesized by converting an alkoxybenzene with chlorosulfuric acid, sulfuric acid/acetic anhydride or the like to a substituted benzene sulfonic acid, then converting it with chlorosulfuric acid, thionyl chloride or the like to a substituted benzene sulfonyl chloride, and reducing it with aluminum lithium hydride, hydrochloric acid/zinc or the like as shown below.

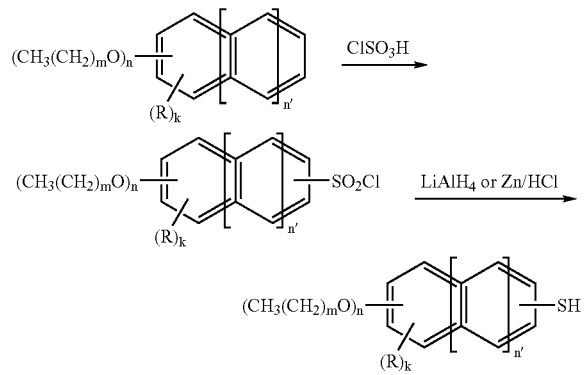

Herein R, m, n, n' and k are as defined above.

Alternatively, a halogenated alkoxybenzene or naphthalene is treated with metallic magnesium to form a Grignard reagent, which is reacted with sulfur and acidified. See Romeo B. Wagner and Harry D. Zook, Synthetic Organic Chemistry, John Wiley & Sons, Inc., 1965, 778–781.

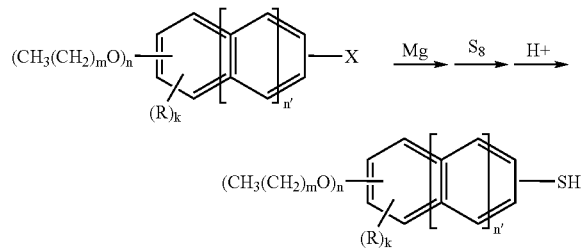

Herein R, m, n, n' and k are as defined above, and X is a halogen atom.

The halogenated alkoxybenzene or naphthalene can be synthesized by reacting a phenol or naphthol derivative with $CH_3(CH_2)_mX$ under basic conditions, followed by reaction with halogen such as bromine. Exemplary of suitable phenol and naphthol derivatives are resorcinol, pyrogallol, hydroquinone, catechol, 4-methylcatechol, 4-ethylresorcinol and dihydroxynaphthalene, with resorcinol, hydroquinone and 4-methylcatechol being preferred.

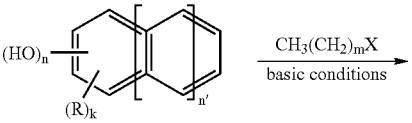

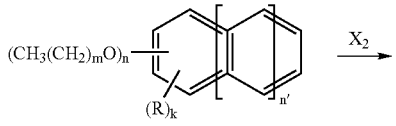

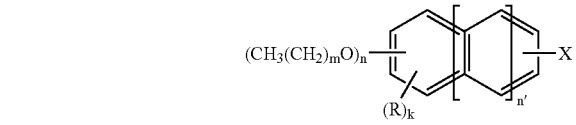

Herein R, m, n, n' and k are as defined above, and X is a halogen atom.

Examples of the sulfonyldiazomethanes of formulae (1) and (1a) include those of the following structures, but are not limited thereto.

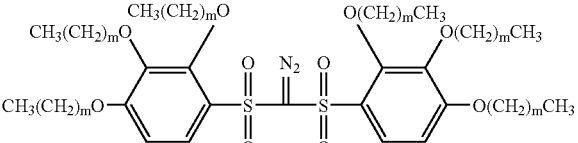

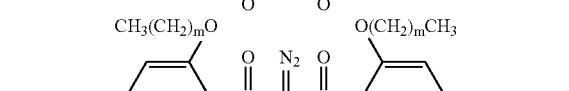

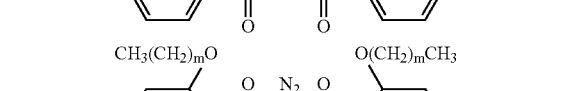

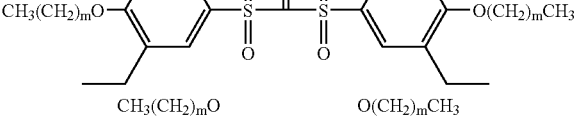

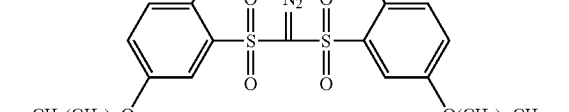

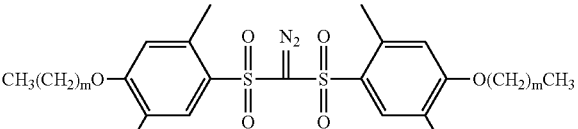

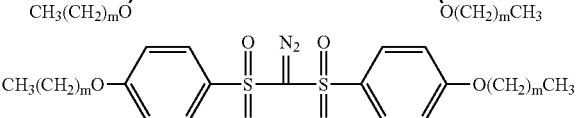

-continued
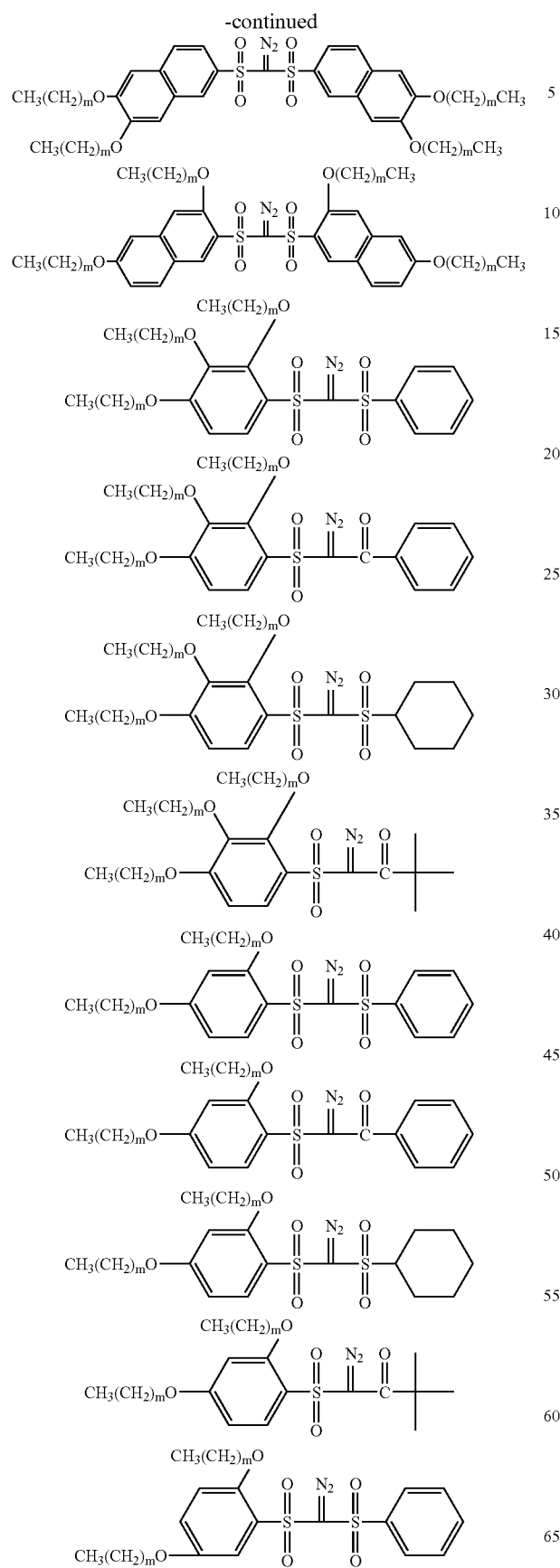
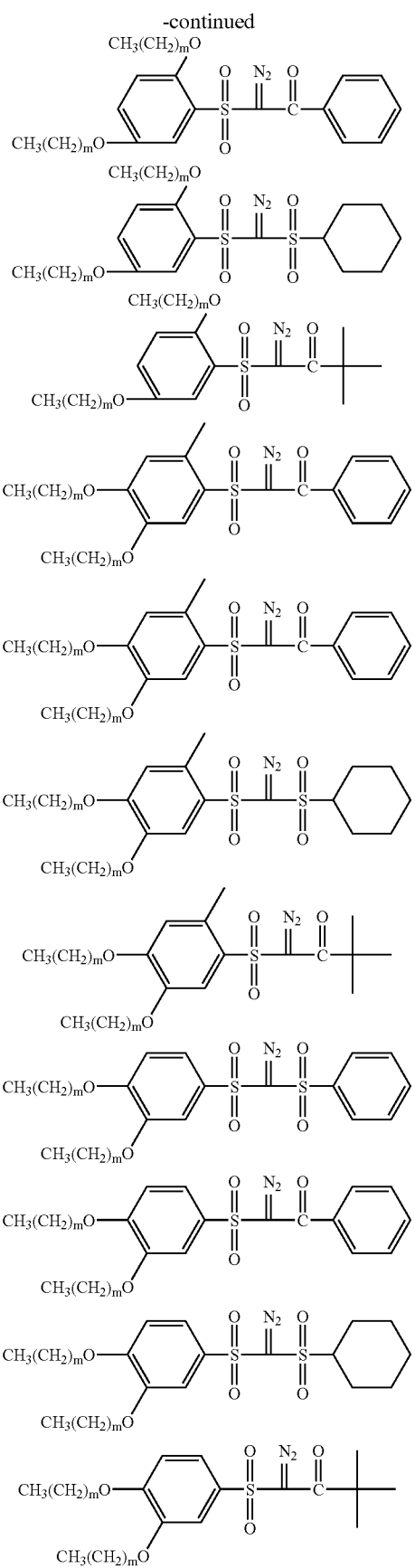

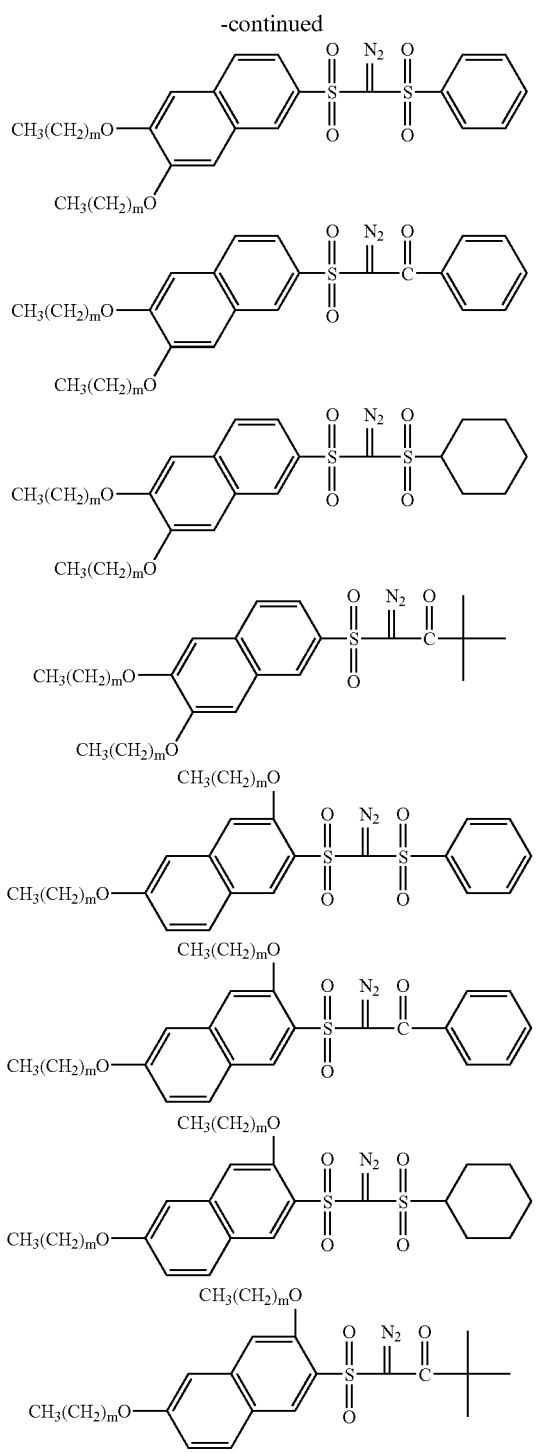

It is noted that m is an integer of 3 to 11.

The sulfonyldiazomethane compounds of formula (1) or (1a) are useful as the photoacid generator in resist materials, especially chemical amplification type resist materials, which are sensitive to radiation such as ultraviolet, deep ultraviolet, electron beams, x-rays, excimer laser light, γ-rays, and synchrotron radiation, for use in the microfabrication of integrated circuits.

Resist Composition

The resist compositions of the invention contain one or more of the sulfonyldiazomethane compounds of formula (1) or (1a). The resist compositions may be either positive or negative working although they are preferably of the chemical amplification type. The resist compositions of the invention include a variety of embodiments, 1) a chemically amplified positive working resist composition comprising (A) a resin which changes its solubility in an alkaline developer under the action of an acid, (B) a sulfonyldiazomethane compound capable of generating an acid upon exposure to radiation represented by the general formula (1) or (1a), and (F) an organic solvent;

2) a chemically amplified positive working resist composition of 1) further comprising (C) a photoacid generator capable of generating an acid upon exposure to radiation other than component (B);

3) a chemically amplified positive working resist composition of 1) or 2) further comprising (D) a basic compound;

4) a chemically amplified positive working resist composition of 1) to 3) further comprising (E) an organic acid derivative;

5) a chemically amplified positive working resist composition of 1) to 4) further comprising (G) a compound with a molecular weight of up to 3,000 which changes its solubility in an alkaline developer under the action of an acid;

6) a chemically amplified negative working resist composition comprising (B) a sulfonyldiazomethane compound capable of generating an acid upon exposure to radiation represented by the general formula (1) or (1a), (F) an organic solvent, (H) an alkali-soluble resin, and (I) an acid crosslinking agent capable of forming a crosslinked structure under the action of an acid;

7) a chemically amplified negative working resist composition of 6) further comprising (C) another photoacid generator;

8) a chemically amplified negative working resist composition of 6) or 7) further comprising (D) a basic compound; and 9) a chemically amplified negative working resist composition of 6) to 8) further comprising (J) an alkali soluble compound having a molecular weight of up to 2,500; but not limited thereto.

Now the respective components are described in detail.

Component (A)

Component (A) is a resin which changes its solubility in an alkaline developer solution under the action of an acid. It is preferably, though not limited to, an alkali-soluble resin having phenolic hydroxyl and/or carboxyl groups in which some or all of the phenolic hydroxyl and/or carboxyl groups are protected with acid-labile protective groups having a C—O—C linkage.

The alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, hydroxyindene, methacrylic acid and acrylic acid, and copolymers having a carboxylic derivative or diphenyl ethylene introduced at the terminus of the foregoing polymers.

Also included are copolymers in which units free of alkali-soluble sites such as styrene, α-methylstyrene, acrylate, methacrylate, hydrogenated hydroxystyrene, maleic anhydride, maleimide, substituted or unsubstituted indene are introduced in addition to the above-described units in such a proportion that the solubility in an alkaline developer may not be extremely reduced. Substituents on the acrylates and methacrylates may be any of the substituents which do not undergo acidolysis. Exemplary substituents are straight, branched or cyclic $C_{1-8}$ alkyl groups and aromatic groups such as aryl groups, but not limited thereto.

Examples of the alkali-soluble resins or polymers are given below. These polymers may also be used as the material from which the resin (A) which changes its solubility in an alkaline developer under the action of an acid is prepared and as the alkali-soluble resin which serves as component (H) to be described later. Examples include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-indene copolymers, p-hydroxystyrene-acrylic acid copolymers, p-hydroxystyrene-methacrylic acid copolymers, p-hydroxystyrene-methyl acrylate copolymers, p-hydroxystyrene-acrylic acid-methyl methacrylate copolymers, p-hydroxystyrene-methyl methacrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-indene copolymers, p-hydroxystyrene-acrylic acid copolymers, and p-hydroxystyrene-methacrylic acid copolymers.

Alkali-soluble resins comprising units of the following formula (2), (2') or (2") are especially preferred.

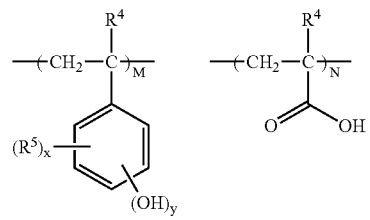

(2')

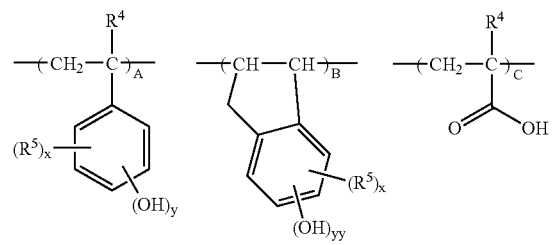

(2")

Herein $R^4$ is hydrogen or methyl, $R^5$ is a straight, branched or cyclic alkyl group of 1 to 8 carbon atoms, x is 0 or a positive integer, y is a positive integer, satisfying $x+y \leq 5$, M and N are positive integers, satisfying $0 < N/(M+N) \leq 0.5$, and A and B are positive integers, and C is 0 or a positive integer, satisfying $0 < B/(A+B+C) \leq 0.5$.

The polymer of formula (2") can be synthesized, for example, by effecting thermal polymerization of an acetoxystyrene monomer, a tertiary alkyl (meth)acrylate monomer and an indene monomer in an organic solvent in the presence of a radical initiator, and subjecting the resulting polymer to alkaline hydrolysis in an organic solvent for deblocking the acetoxy group, for thereby forming a ternary copolymer of hydroxystyrene, tertiary alkyl (meth)acrylate and indene. The organic solvent used during polymerization is exemplified by toluene, benzene, tetrahydrofuran, diethyl ether and dioxane. Exemplary polymerization initiators include 2,2'-azobisisobutyronitrile, 2,2'-azobis(2,4-dimethylvaleronitrile), dimethyl-2,2-azobis(2-methylpropionate), benzoyl peroxide, and lauroyl peroxide. Polymerization is preferably effected while heating at 50 to 80° C. The reaction time is usually about 2 to 100 hours, preferably about 5 to 20 hours. Aqueous ammonia, triethylamine or the like may be used as the base for the alkaline hydrolysis. For the alkaline hydrolysis, the temperature is usually −20° C. to 100° C., preferably 0° C. to 60° C., and the time is about 0.2 to 100 hours, preferably about 0.5 to 20 hours.

Also included are polymers having the dendritic or hyperbranched polymer structure of formula (2''') below.

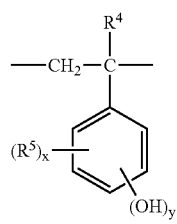

(2)

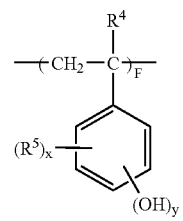

(2''')

-continued

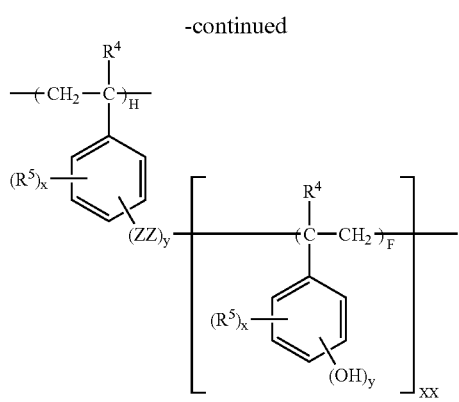

Herein ZZ is a divalent organic group selected from among $CH_2$, $CH(OH)$, $CR^5(OH)$, $C=O$ and $C(OR^5)(OH)$ or a trivalent organic group represented by $-C(OH)=$. Subscript F, which may be identical or different, is a positive integer, and H is a positive integer, satisfying $0.001 \leq H/(H+F) \leq 0.1$, and XX is 1 or 2. $R^4$, $R^5$, x and y are as defined above.

The dendritic or hyperbranched polymer of phenol derivative can be synthesized by effecting living anion polymerization of a polymerizable monomer such as 4-tert-butoxystyrene and reacting a branching monomer such as chloromethylstyrene as appropriate during the living anion polymerization. For the detail of synthesis, reference is made to JP-A 2000-344836.

The alkali-soluble resins or polymers should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

In the resist composition using the sulfonyldiazomethane of formula (1), a resin having such substituent groups with C—O—C linkages (acid labile groups) that the solubility in an alkaline developer changes as a result of severing of the C—O—C linkages under the action of an acid, especially an alkali-soluble resin as mentioned above is preferably used as component (A). Especially preferred is a polymer comprising recurring units of the above formula (2) and containing phenolic hydroxyl groups in which hydrogen atoms of the phenolic hydroxyl groups are substituted with acid labile groups of one or more types in a proportion of more than 0 mol % to 80 mol % on the average of the entire hydrogen atoms of the phenolic hydroxyl group, the polymer having a weight average molecular weight of 3,000 to 100,000.

Also preferred is a polymer comprising recurring units of the above formula (2'), that is, a copolymer comprising p-hydroxystyrene and/or α-methyl-p-hydroxystyrene and acrylic acid and/or methacrylic acid, wherein some of the hydrogen atoms of the carboxyl groups of acrylic acid and/or methacrylic acid are substituted with acid labile groups of one or more types, and the units derived from acrylate and/or methacrylate are contained in a proportion of more than 0 mol % to 50 mol %, on the average, of the copolymer, and wherein some of the hydrogen atoms of the phenolic hydroxyl groups of p-hydroxystyrene and/or α-methyl-p-hydroxystyrene may be substituted with acid labile groups of one or more types. In the preferred copolymer, the units derived from acrylate and/or methacrylate and the units derived from p-hydroxystyrene and/or α-methyl-p-hydroxystyrene optionally having acid labile groups substituted thereon are contained in a proportion of more than 0 mol % to 80 mol %, on the average, of the copolymer.

Alternatively, a polymer comprising recurring units of the above formula (2"), that is, a copolymer comprising p-hydroxystyrene and/or α-methyl-p-hydroxystyrene and substituted and/or unsubstituted indene, is preferred wherein some of the hydrogen atoms of the phenolic hydroxyl groups of p-hydroxystyrene and/or α-methyl-p-hydroxystyrene are substituted with acid labile groups of one or more types, and some of the hydrogen atoms of the carboxyl groups of acrylic acid and/or methacrylic acid are substituted with acid labile groups of one or more types. Where the substituted indene has hydroxyl groups, some of the hydrogen atoms of these hydroxyl groups may be substituted with acid labile groups of one or more types. In the preferred copolymer, the units derived from p-hydroxystyrene and/or α-methyl-p-hydroxystyrene having acid labile groups substituted thereon, the units derived from acrylic acid and/or methacrylic acid having acid labile groups substituted thereon, and the units derived from indene having acid labile groups substituted thereon are contained in a proportion of more than 0 mol % to 80 mol %, on the average, of the copolymer.

Exemplary and preferred such polymers are polymers or high molecular weight compounds comprising recurring units represented by the following general formula (2a), (2a') or (2a") and having a weight average molecular weight of 3,000 to 100,000.

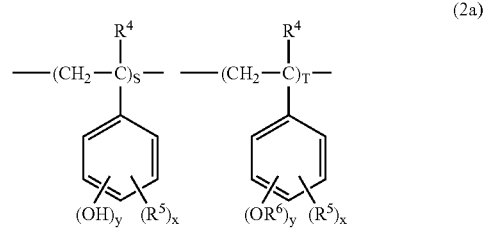

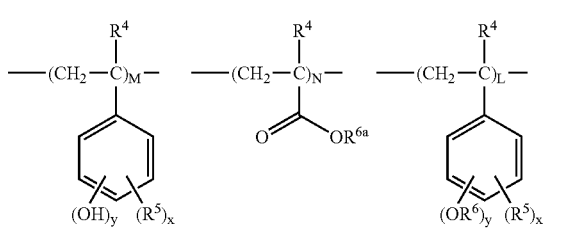

-continued

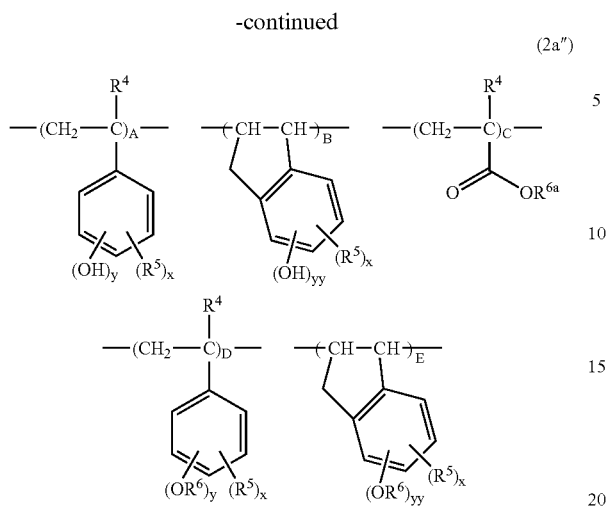

(2a″)

Herein, $R^4$ is hydrogen or methyl. $R^5$ is a straight, branched or cyclic alkyl group of 1 to 8 carbon atoms. Letter x is 0 or a positive integer, and y is a positive integer, satisfying $x+y \leqq 5$. $R^6$ is an acid labile group. S and T are positive integers, satisfying $0 < T/(S+T) \leqq 0.8$. $R^{6a}$ is hydrogen or an acid labile group, at least some of the $R^{6a}$ groups are acid labile groups. M and N are positive integers, L is 0 or a positive integer, satisfying $0 < N/(M+N+L) \leqq 0.5$ and $0 \leqq (N+L)/(M+N+L) \leqq 0.5$. The letter yy is 0 or a positive integer, satisfying $x+yy \leqq 5$. A and B are positive integers, C, D and E each are 0 or a positive integer, satisfying $0 < (B+E)/(A+B+C+D+E) \leqq 0.5$ and $0 < (C+D+E)/(A+B+C+D+E) \leqq 0.8$.

$R^5$ stands for straight, branched or cyclic $C_{1-8}$ alkyl groups, for example, methyl, ethyl, propyl, isopropyl, n-butyl, isobutyl, tert-butyl, cyclohexyl and cyclopentyl.

With respect to the acid labile groups, where some of the phenolic hydroxyl groups and some or all of the carboxyl groups in the alkali-soluble resin are protected with acid labile groups having C—O—C linkages, the acid labile groups are selected from a variety of such groups. The preferred acid labile groups are groups of the following general formulae (4) to (7), tertiary alkyl groups of 4 to 20 carbon atoms, preferably 4 to 15 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms.

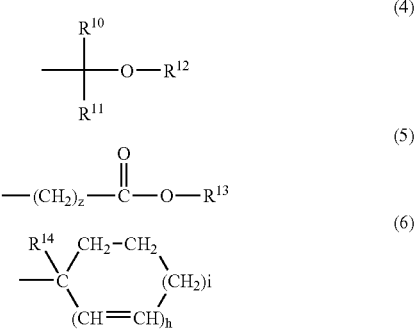

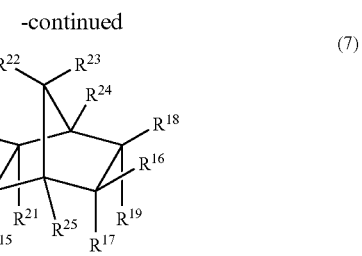

Herein $R^{10}$ and $R^{11}$ are independently hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{12}$ is a monovalent hydrocarbon group of 1 to 18 carbon atoms, preferably 1 to 10 carbon atoms, which may have a hetero atom (e.g., oxygen atom), for example, straight, branched or cyclic alkyl groups, and such groups in which some hydrogen atoms are substituted with hydroxyl, alkoxy, oxo, amino or alkylamino groups. Illustrative examples of the substituted alkyl groups are given below.

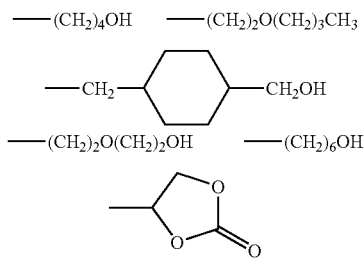

A pair of $R^{10}$ and $R^{11}$, a pair of $R^{10}$ and $R^{12}$, or a pair of $R^{11}$ and $R^{12}$, taken together, may form a ring. Each of $R^{10}$, $R^{11}$ and $R^{12}$ is a straight or branched alkylene group of 1 to 18 carbon atoms, preferably 1 to 10 carbon atoms, when they form a ring.

$R^{13}$ is a tertiary alkyl group of 4 to 20 carbon atoms, preferably 4 to 15 carbon atoms, a trialkylsilyl group whose alkyl groups each have 1 to 6 carbon atoms, an oxoalkyl group of 4 to 20 carbon atoms or a group of formula (4). Exemplary tertiary alkyl groups are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl and 1-adamantyl-1-methylethyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-5-oxooxolan-4-yl. Letter z is an integer of 0 to 6.

$R^{14}$ is a straight, branched or cyclic alkyl group of 1 to 8 carbon atoms or substituted or unsubstituted aryl group of 6 to 20 carbon atoms. Exemplary straight, branched or cyclic alkyl groups include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl and cyclohexylethyl. Exemplary substituted or unsubstituted aryl groups include phenyl, methylphenyl, naphthyl, anthryl, phenanthryl, and pyrenyl. Letter h is equal to 0 or 1, i is equal to 0, 1, 2 or 3, satisfying 2h+i=2 or 3.

$R^{15}$ is a straight, branched or cyclic alkyl group of 1 to 8 carbon atoms or substituted or unsubstituted aryl group of 6 to 20 carbon atoms, examples of which are as exemplified for $R^{14}$. $R^{16}$ to $R^{25}$ are independently hydrogen or monovalent hydrocarbon groups of 1 to 15 carbon atoms which may contain a hetero atom, for example, straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and substituted ones of these groups in which some hydrogen atoms are substituted with hydroxyl, alkoxy, carboxy, alkoxycarbonyl, oxo, amino, alkylamino, cyano, mercapto, alkylthio, and sulfo groups. $R^{16}$ to $R^{25}$, for example, a pair of $R^{16}$ and $R^{17}$, a pair of $R^{16}$ and $R^{18}$, a pair of $R^{17}$ and $R^{19}$, a pair of $R^{18}$ and $R^{19}$, a pair of $R^{20}$ and $R^{21}$, or a pair of $R^{22}$ and $R^{23}$, taken together, may form a ring. When $R^{16}$ to $R^{26}$ form a ring, they are divalent hydrocarbon groups of 1 to 15 carbon atoms which may contain a hetero atom, examples of which are the above-exemplified monovalent hydrocarbon groups with one hydrogen atom eliminated. Also, two of $R^{16}$ to $R^{25}$ which are attached to adjacent carbon atoms (for example, a pair of $R^{16}$ and $R^{18}$, a pair of $R^{18}$ and $R^{24}$, or a pair of $R^{22}$ and $R^{24}$) may directly bond together to form a double bond.

Of the acid labile groups of formula (4), illustrative examples of the straight or branched groups are given below.

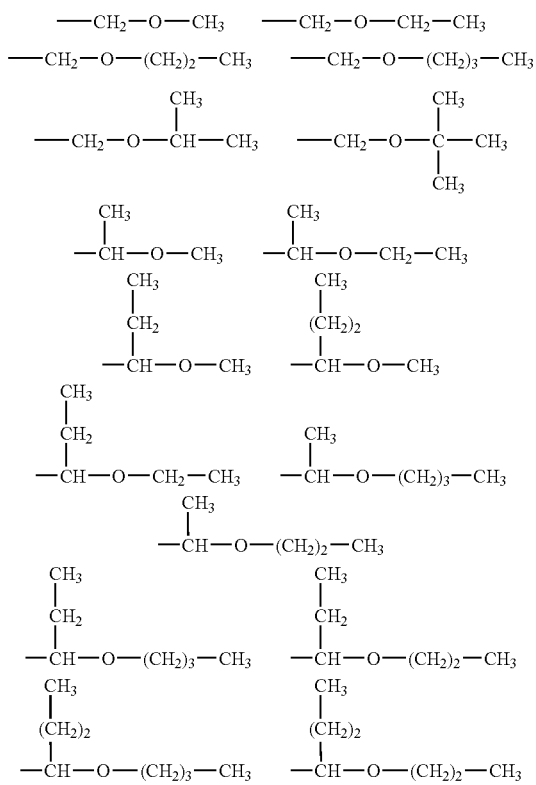

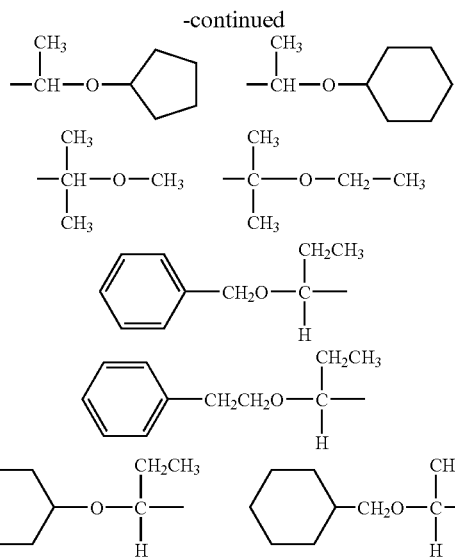

Of the acid labile groups of formula (4), illustrative examples of the cyclic groups include tetrahydrofuran-2-yl, 2-methyltetrahydrofuran-2-yl, tetrahydropyran-2-yl and 2-methyltetrahydropyran-2-yl.

Illustrative examples of the acid labile groups of formula (5) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Illustrative examples of the acid labile groups of formula (6) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, 3-ethyl-1-cyclohexen-3-yl, and 1-cyclohexyl-cyclopentyl.

Illustrative examples of the acid labile groups of formula (7) are given below.

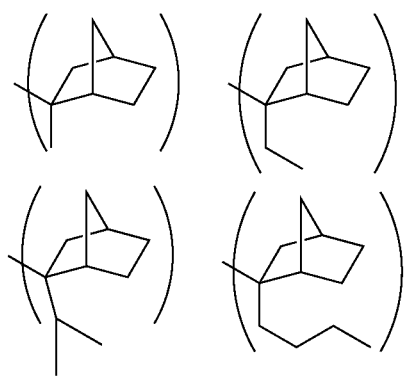

-continued

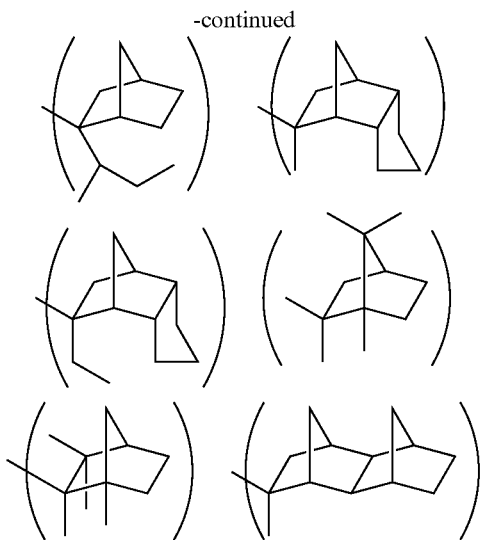

Exemplary of the tertiary alkyl group of 4 to 20 carbon atoms, preferably 4 to 15 carbon atoms, are tert-butyl, tert-amyl, 3-ethyl-3-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, 1-adamantyl-1-methylethyl, 3-ethyl-3-pentyl and dimethylbenzyl.

Exemplary of the trialkylsilyl groups whose alkyl groups each have 1 to 6 carbon atoms are trimethylsilyl, triethylsilyl, and tert-butyldimethylsilyl.

Exemplary of the oxoalkyl groups of 4 to 20 carbon atoms are 3-oxocyclohexyl and groups represented by the following formulae.

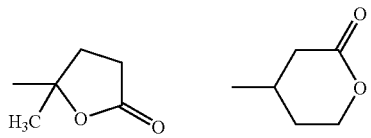

Exemplary of the aryl-substituted alkyl groups of 7 to 20 carbon atoms are benzyl, methylbenzyl, dimethylbenzyl, diphenylmethyl, and 1,1-diphenylethyl.

In the resist composition comprising the sulfonyldiazomethane as a photoacid generator, the resin (A) which changes its solubility in an alkaline developer under the action of an acid may be the polymer of formula (2) or (2'), (2") or (2''') in which some of the hydrogen atoms of the phenolic hydroxyl groups are crosslinked within a molecule and/or between molecules, in a proportion of more than 0 mol % to 50 mol %, on the average, of the entire phenolic hydroxyl groups on the polymer, with crosslinking groups having C—O—C linkages represented by the following general formula (3). With respect to illustrative examples and synthesis of polymers crosslinked with acid labile groups, reference should be made to JP-A 11-190904.

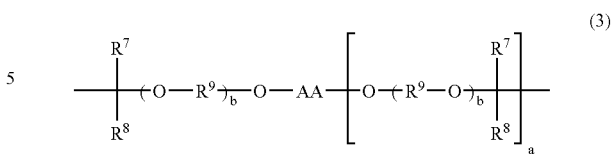

Herein, each of $R^7$ and $R^8$ is hydrogen or a straight, branched or cyclic alkyl group of 1 to 8 carbon atoms, or $R^7$ and $R^8$, taken together, may form a ring, and each of $R^7$ and $R^8$ is a straight or branched alkylene group of 1 to 8 carbon atoms when they form a ring. $R^9$ is a straight, branched or cyclic alkylene group of 1 to 10 carbon atoms. Letter "b" is 0 or an integer of 1 to 10. AA is an a-valent aliphatic or alicyclic saturated hydrocarbon group, aromatic hydrocarbon group or heterocyclic group of 1 to 50 carbon atoms, which may be separated by a hetero atom and in which some of the hydrogen atom attached to carbon atoms may be substituted with hydroxyl, carboxyl, carbonyl or halogen. Letter "a" is an integer of 1 to 7.

Preferably in formula (3), $R^7$ is methyl, $R^8$ is hydrogen, "a" is 1, "b" is 0, and AA is ethylene, 1,4-butylene or 1,4-cyclohexylene.

It is noted that these polymers which are crosslinked within the molecule or between molecules with crosslinking groups having C—O—C linkages can be synthesized by reacting a corresponding non-crosslinked polymer with an alkenyl ether in the presence of an acid catalyst in a conventional manner.

If decomposition of other acid labile groups proceeds under acid catalyst conditions, the end product can be obtained by once reacting the alkenyl ether with hydrochloric acid or the like for conversion to a halogenated alkyl ether and reacting it with the polymer under basic conditions in a conventional manner.

Illustrative, non-limiting, examples of the alkenyl ether include ethylene glycol divinyl ether, triethylene glycol divinyl ether, 1,2-propanediol divinyl ether, 1,3-propanediol divinyl ether, 1,3-butanediol divinyl ether, 1,4-butanediol divinyl ether, neopentyl glycol divinyl ether, trimethylolpropane trivinyl ether, trimethylolethane trivinyl ether, hexanediol divinyl ether, and 1,4-cyclohexanediol divinyl ether.

In the chemical amplification type positive resist composition, the resin used as component (A) is as described above while the preferred acid labile groups to be substituted for phenolic hydroxyl groups are 1-ethoxyethyl, 1-ethoxypropyl, tetrahydrofuranyl, tetrahydropyranyl, tert-butyl, tert-amyl, 1-ethylcyclohexyloxycarbonylmethyl, tert-butoxycarbonyl, tert-butoxycarbonylmethyl, and substituents of formula (3) wherein $R^7$ is methyl, $R^8$ is hydrogen, "a" is 1, "b" is 0, and AA is ethylene, 1,4-butylene or 1,4-cyclohexylene. Also preferably, the hydrogen atoms of carboxyl groups of methacrylic acid or acrylic acid are protected with substituent groups as typified by tert-butyl, tert-amyl, 2-methyl-2-adamantyl, 2-ethyl-2-adamantyl, 1-ethylcyclopentyl, 1-ethylcyclohexyl, 1-cyclohexylcyclopentyl, 1-ethylnorbornyl, tetrahydrofuranyl and tetrahydropyranyl.

In a single polymer, these substituents may be incorporated alone or in admixture of two or more types. A blend of two or more polymers having substituents of different types is also acceptable.

The percent proportion of these substituents substituting for phenol and carboxyl groups in the polymer is not critical. Preferably the percent substitution is selected such that when a resist composition comprising the polymer is applied onto a substrate to form a coating, the unexposed area of the coating may have a dissolution rate of 0.01 to 10 Å/sec in a 2.38% tetramethylammonium hydroxide (TMAH) developer.

On use of a polymer containing a greater proportion of carboxyl groups which can reduce the alkali dissolution rate, the percent substitution must be increased or non-acid-decomposable substituents to be described later must be introduced.

When acid labile groups for intramolecular and/or intermolecular crosslinking are to be introduced, the percent proportion of crosslinking substituents is preferably up to 20 mol %, more preferably up to 10 mol %, based on the entire hydrogen atoms of phenolic hydroxyl groups. If the percent substitution of crosslinking substituents is too high, crosslinking results in a higher molecular weight which can adversely affect dissolution, stability and resolution. It is also preferred to further introduce another non-crosslinking acid labile group into the crosslinked polymer at a percent substitution of up to 10 mol % for adjusting the dissolution rate to fall within the above range.

In the case of poly(p-hydroxystyrene), the optimum percent substitution differs between a substituent having a strong dissolution inhibitory action such as a tert-butoxycarbonyl group and a substituent having a weak dissolution inhibitory action such as an acetal group although the overall percent substitution is preferably 10 to 40 mol %, more preferably 20 to 30 mol %, based on the entire hydrogen atoms of phenolic hydroxyl groups in the polymer.

Polymers having such acid labile groups introduced therein should preferably have a weight average molecular weight (Mw) of 3,000 to 100,000. With a Mw of less than 3,000, polymers would perform poorly and often lack heat resistance and film formability. Polymers with a Mw of more than 100,000 would be less soluble in a developer and a resist solvent.

Where non-crosslinking acid labile groups are introduced, the polymer should preferably have a dispersity (Mw/Mn) of up to 3.5, preferably up to 1.5. A polymer with a dispersity of more than 3.5 often results in a low resolution. Where crosslinking acid labile groups are introduced, the starting alkali-soluble resin should preferably have a dispersity (Mw/Mn) of up to 1.5, and the dispersity is kept at 3 or lower even after protection with crosslinking acid labile groups. If the dispersity is higher than 3, dissolution, coating, storage stability and/or resolution is often poor.

To impart a certain function, suitable substituent groups may be introduced into some of the phenolic hydroxyl and carboxyl groups on the acid labile group-protected polymer. Exemplary are substituent groups for improving adhesion to the substrate, non-acid-labile groups for adjusting dissolution in an alkali developer, and substituent groups for improving etching resistance. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, propyl, n-butyl, sec-butyl, acetyl, pivaloyl, adamantyl, isoboronyl, and cyclohexyl.

In the resist composition of the invention, the above-described resin is added in any desired amount, and usually 65 to 99 parts by weight, preferably 70 to 98 parts by weight per 100 parts by weight of the solids in the composition. The term "solids" is used to encompass all components in the resist composition excluding the solvent.

Illustrative examples of the sulfonyldiazomethane compounds of formulae (1) and (1a) as the photoacid generator (B) are as described above. Listing again, examples of bilaterally symmetric bissulfonyldiazomethane include, but are not limited to, bis(2,3,4-tri(n-butyloxy)benzenesulfonyl)diazomethane, bis(2,3,4-tri(n-pentyloxy)benzenesulfonyl)diazomethane, bis(2,3,4-tri(n-hexyloxy)benzenesulfonyl)diazomethane, bis(2,3,4-tri(n-heptyloxy)benzenesulfonyl)diazomethane, bis(2,3,4-tri(n-octyloxy)benzenesulfonyl)diazomethane, bis(2,3,4-tri(n-decyloxy)benzenesulfonyl)diazomethane, bis(2,3,4-tri(n-dodecyloxy)benzenesulfonyl)diazomethane, bis(2,4-di(n-butyloxy)benzenesulfonyl)diazomethane, bis(2,4-di(n-pentyloxy)benzenesulfonyl)diazomethane, bis(2,4-di(n-hexyloxy)benzenesulfonyl)diazomethane, bis(2,4-di(n-heptyloxy)benzenesulfonyl)diazomethane, bis(2,4-di(n-octyloxy)benzenesulfonyl)diazomethane, bis(2,4-di(n-decyloxy)benzenesulfonyl)diazomethane, bis(2,4-di(n-dodecyloxy)benzenesulfonyl)diazomethane, bis(2,4-di(n-butyloxy)-5-ethylbenzenesulfonyl)diazomethane, bis(2,4-di(n-pentyloxy)-5-ethylbenzenesulfonyl)diazomethane, bis(2,4-di(n-hexyloxy)-5-ethylbenzenesulfonyl)diazomethane, bis(2,4-di(n-heptyloxy)-5-ethylbenzenesulfonyl)diazomethane, bis(2,4-di(n-octyloxy)-5-ethylbenzenesulfonyl)diazomethane, bis(2,4-di(n-decyloxy)-5-ethylbenzenesulfonyl)diazomethane, bis(2,4-di(n-dodecyloxy)-5-ethylbenzenesulfonyl)diazomethane, bis(2,5-di(n-butyloxy)benzenesulfonyl)diazomethane, bis(2,5-di(n-pentyloxy)benzenesulfonyl)diazomethane, bis(2,5-di(n-hexyloxy)benzenesulfonyl)diazomethane, bis(2,5-di(n-heptyloxy)benzenesulfonyl)diazomethane, bis(2,5-di(n-octyloxy)benzenesulfonyl)diazomethane, bis(2,5-di(n-decyloxy)benzenesulfonyl)diazomethane, bis(2,5-di(n-dodecyloxy)benzenesulfonyl)diazomethane, bis(3,4-di(n-butyloxy)benzenesulfonyl)diazomethane, bis(3,4-di(n-pentyloxy)benzenesulfonyl)diazomethane, bis(3,4-di(n-hexyloxy)benzenesulfonyl)diazomethane, bis(3,4-di(n-heptyloxy)benzenesulfonyl)diazomethane, bis(3,4-di(n-octyloxy)benzenesulfonyl)diazomethane, bis(3,4-di(n-decyloxy)benzenesulfonyl)diazomethane, bis(3,4-di(n-dodecyloxy)benzenesulfonyl)diazomethane, bis(3,4-di(n-butyloxy)-6-methylbenzenesulfonyl)diazomethane, bis(3,4-di(n-pentyloxy)-6-methylbenzenesulfonyl)diazomethane, bis(3,4-di(n-hexyloxy)-6-methylbenzenesulfonyl)diazomethane, bis(3,4-di(n-heptyloxy)-6-methylbenzenesulfonyl)diazomethane, bis(3,4-di(n-octyloxy)-6-methylbenzenesulfonyl)diazomethane, bis(3,4-di(n-decyloxy)-6-methylbenzenesulfonyl)diazomethane, bis(3,4-di(n-dodecyloxy)-6-methylbenzenesulfonyl)diazomethane, bis (6,7-di(n-butyloxy)-2-naphthalenesulfonyl)diazomethane, bis(6,7-di(n-pentyloxy)-2-naphthalenesulfonyl)diazomethane, bis(6,7-di(n-hexyloxy)-2-naphthalenesulfonyl)diazomethane, bis(6,7-di(n-heptyloxy)-2-naphthalenesulfonyl)diazomethane, bis(6,7-di(n-octyloxy)-2-naphthalenesulfonyl)diazomethane, bis(6,7-di(n-decyloxy)-2-naphthalenesulfonyl)diazomethane, bis(6,7-di(n-dodecyloxy)-2-naphthalenesulfonyl)diazomethane, bis(3,6-di(n-butyloxy)-2-naphthalenesulfonyl)diazomethane, bis(3,6-di(n-pentyloxy)-2-naphthalenesulfonyl)diazomethane, bis(3,6-di(n-hexyloxy)-2-naphthalenesulfonyl)diazomethane, bis(3,6-di(n-heptyloxy)-2-naphthalenesulfonyl)diazomethane, bis(3,6-di(n-octyloxy)-2-naphthalenesulfonyl)diazomethane, bis(3,6-di(n-decyloxy)-2-naphthalenesulfonyl)diazomethane, bis(3,6-di(n-dodecyloxy)-2-naphthalenesulfonyl)diazomethane, etc. Of these, preferred are bis(3,4-di(n-butyloxy)-6-methylbenzenesulfonyl)diazomethane, bis(3,4-di(n-pentyloxy)-6-methylbenzenesulfonyl)diazomethane, and bis(3,4-di(n-hexyloxy)-6-methylbenzenesulfonyl)diazomethane.

Examples of bilaterally asymmetric sulfonyldiazomethane include, but are not limited to, 2,3,4-tri(n-butyloxy)benzenesulfonyl-cyclohexylsulfonyldiazomethane, 2,3,4-tri(n-butyloxy)benzenesulfonyl-benzenesulfonyldiazomethane, 2,3,4-tri(n-hexyloxy)benzenesulfonyl-(2-methyl)benzenesulfonyldiazomethane, 2,4-di(n-butyloxy)benzenesulfonyl-cyclohexylsulfonyldiazomethane, 2,4-di(n-pentyloxy)benzenesulfonyl-benzenesulfonyldiazomethane, 2,4-di(n-hexyloxy)benzenesulfonyl-(2-methyl)benzenesulfonyldiazomethane, 2,5-di(n-butyloxy)benzenesulfonyl-cyclohexylsulfonyldiazomethane, 2,5-di(n-pentyloxy)benzenesulfonyl-benzenesulfonyldiazomethane, 2,5-di(n-hexyloxy)benzenesulfonyl-(2-methyl)benzenesulfonyldiazomethane, 3,4-di(n-butyloxy)benzenesulfonyl-cyclohexylsulfonyldiazomethane, 3,4-di(n-pentyloxy)benzenesulfonyl-benzenesulfonyldiazomethane, 3,4-di(n-hexyloxy)benzenesulfonyl-(2-methyl)benzenesulfonyldiazomethane, 3,4-di(n-butyloxy)-6-methylbenzenesulfonyl-cyclohexylsulfonyldiazomethane, 3,4-di(n-pentyloxy)-6-methylbenzenesulfonyl-benzenesulfonyldiazomethane, 3,4-di(n-hexyloxy)-6-methylbenzenesulfonyl-(2-methyl)benzenesulfonyldiazomethane, 6,7-di(n-butyloxy)-2-naphthalenesulfonyl-cyclohexylsulfonyldiazomethane, 6,7-di(n-pentyloxy)-2-naphthalenesulfonyl-benzenesulfonyldiazomethane, 6,7-di(n-hexyloxy)-2-naphthalenesulfonyl-(2-methyl)benzenesulfonyldiazomethane, 3,6-di(n-butyloxy)-2-naphthalenesulfonyl-cyclohexylsulfonyldiazomethane, 3,6-di(n-pentyloxy)-2-naphthalenesulfonyl-benzenesulfonyldiazomethane, 3,6-di(n-hexyloxy)-2-naphthalenesulfonyl-(2-methyl)benzenesulfonyldiazomethane, etc.

Examples of the sulfonyl-carbonyldiazomethane include, but are not limited to, 2,3,4-tri(n-butyloxy)benzenesulfonyl-tert-butylcarbonyldiazomethane, 2,3,4-tri(n-butyloxy)benzenesulfonyl-benzenecarbonyldiazomethane, 2,3,4-tri(n-hexyloxy)benzenesulfonyl-2-naphthalenecarbonyldiazomethane, 2,4-di(n-butyloxy)benzenesulfonyl-tert-butylcarbonyldiazomethane, 2,4-di(n-pentyloxy)benzenesulfonyl-benzenecarbonyldiazomethane, 2,4-di(n-hexyloxy)benzenesulfonyl-2-naphthalenecarbonyldiazomethane, 2,5-di(n-butyloxy)benzenesulfonyl-tert-butylcarbonyldiazomethane, 2,5-di(n-pentyloxy)benzenesulfonyl-benzenecarbonyldiazomethane, 2,5-di(n-hexyloxy)benzenesulfonyl-2-naphthalenecarbonyldiazomethane, 3,4-di(n-butyloxy)benzenesulfonyl-tert-butylcarbonyldiazomethane, 3,4-di(n-pentyloxy)benzenesulfonyl-benzenecarbonyldiazomethane, 3,4-di(n-hexyloxy)benzenesulfonyl-2-naphthalenecarbonyldiazomethane, 3,4-di(n-butyloxy)-6-methylbenzenesulfonyl-tert-butylcarbonyldiazomethane, 3,4-di(n-pentyloxy)-6-methylbenzenesulfonyl-benzenecarbonyldiazomethane, 3,4-di(n-hexyloxy)-6-methylbenzenesulfonyl-2-naphthalenecarbonyldiazomethane, 6,7-di(n-butyloxy)-2-naphthalenesulfonyl-tert-butylcarbonyldiazomethane, 6,7-di(n-pentyloxy)-2-naphthalenesulfonyl-benzenecarbonyldiazomethane, 6,7-di(n-hexyloxy)-2-naphthalenesulfonyl-2-naphthalenecarbonyldiazomethane, etc.

In the chemical amplification resist composition an appropriate amount of the sulfonyldiazomethane compound of formula (1) or (1a) added is from more than 0 part to 10 parts by weight, and preferably from 1 to 5 parts by weight, per 100 parts by weight of the solids in the composition. The sulfonyldiazomethane compound is used at least in an amount to generate a sufficient amount of acid to deblock acid labile groups in the polymer. Too large amounts may excessively reduce the transmittance of resist film, failing to form a rectangular pattern, and give rise to problems of abnormal particles and deposits during resist storage. The photoacid generators may be used alone or in admixture of two or more.

Component (C)

In one preferred embodiment, the resist composition further contains (C) a compound capable of generating an acid upon exposure to high energy radiation, that is, a second photoacid generator other than the sulfonyldiazomethane (B) having formula (1) or (1a). Suitable second photoacid generators include sulfonium salts, iodonium salts, sulfonyldiazomethane and N-sulfonyloxyimide photoacid generators. Exemplary second photoacid generators are given below while they may be used alone or in admixture of two or more.

Sulfonium salts are salts of sulfonium cations with sulfonates. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, and 2-oxo-2-phenylethylthiacyclopentanium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, naphthalenesulfonate, camphorsulfonate, octanesulfonate, dodecylbenzenesulfonate, butanesulfonate, and methanesulfonate. Sulfonium salts based on combination of the foregoing examples are included.

Iodinium salts are salts of iodonium cations with sulfonates. Exemplary iodinium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, and methanesulfonate. Iodonium salts based on combination of the foregoing examples are included.

Exemplary sulfonyldiazomethane compounds include bissulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(2-naphthylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo[2.2.1]-5-heptene-2,3-dicarboxylic acid imide. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, and methanesulfonate.

Benzoinsulfonate photoacid generators include benzoin tosylate, benzoin mesylate, and benzoin butanesulfonate.

Pyrogallol trisulfonate photoacid generators include pyrogallol, fluoroglycine, catechol, resorcinol, hydroquinone, in which all the hydroxyl groups are substituted with trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate. Also useful are analogous nitrobenzyl sulfonate compounds in which the nitro group on the benzyl side is substituted with a trifluoromethyl group.

Sulfone photoacid generators include bis (phenylsulfonyl) methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl) propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives are described in Japanese Patent No. 2,906,999 and JP-A 9-301948 and include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(p-fluorobenzenesulfonyl)-nioxime, bis-O-(p-trifluoromethylbenzenesulfonyl)-nioxime, and bis-O-(xylenesulfonyl)-nioxime.

Also included are the oxime sulfonates described in U.S. Pat. No. 6,004,724, for example, (5-(4-toluenesulfonyl)oxy-imino-5H-thiophen-2-ylidene)phenylacetonitrile, (5-(10-camphorsulfonyl)oxyimino-5H-thiophen-2-ylidene)phenylacetonitrile, (5-n-octanesulfonyloxyimino-5H-thiophen-2-ylidene)phenylacetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)-sulfonate; 2,2,2-trifluoro-1-(phenyl)-ethanone oxime-O-(2-naphthyl)-sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)sulfonate; 2,2,2-trifluoro-1-(4-methoxyphenyl)-ethanone oxime-O-octylsulfonate; 2,2,2-trifluoro-1-(4-thiomethylphenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethylphenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenyl-sulfonate; 2,2,2-trifluoro-1-(4-chlorophenyl)-ethanone oxime-O-phenyl-sulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propylsulfonate; 2,2,2-trifluoro-1-[4-methylsulfonylphenyl]-ethanone oxime-O-propylsulfonate; 1,3-bis[1-(4-phenoxyphenyl)-2,2,2-trifluoroethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; and 2,2,2-trifluoro-1-[1-dioxa-thiophen-2-yl)]-ethanone oxime-O-propylsulfonate.

Also included are the oxime sulfonates described in JP-A 9-95479 and JP-A 9-230588 and the references cited therein, for example, α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylacetonitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl]acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Suitable bisoxime sulfonates include those described in JP-A 9-208554, for example, bis(α-(4-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(4-toluenesulfonyloxy)imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediacetonitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylenediacetonitrile, bis(α-(4-methoxybenzenesulfonyloxy)imino)-m-phenylenediacetonitrile, etc.

Of these, preferred photoacid generators are sulfonium salts, bissulfonyldiazomethanes, N-sulfonyloxyimides and glyoxime derivatives. More preferred photoacid generators are sulfonium salts, bissulfonyldiazomethanes, and N-sulfonyloxyimides. Typical examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluenesulfonyloxy)benzenesulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-tert-butylphenylsulfonyl)diazomethane, N-camphorsulfonyloxy-5-norbornene-2,3-carboxylic acid imide, and N-p-toluenesulfonyloxy-5-norbornene-2,3-carboxylic acid imide.

In the resist composition comprising the sulfonyldiazomethane of formula (1) or (1a) as the first photoacid generator according to the invention, the second photoacid generator (C) may be used in any desired amount as long as it does not compromise the effects of the sulfonyldiazomethane of formula (1) or (1a). An appropriate amount of the second photoacid generator (C) is 0 to 10 parts, and especially 0 to 5 parts by weight per 100 parts by weight of the solids in the composition. Too high a proportion of the second photoacid generator (C) may give rise to problems of degraded resolution and foreign matter upon development and resist film peeling. The second photoacid generators may be used alone or in admixture of two or more. The transmittance of the resist film can be controlled by using a (second) photoacid generator having a low transmittance at the exposure wavelength and adjusting the amount of the photoacid generator added.

In the resist composition comprising the sulfonyldiazomethane as the photoacid generator according to the invention, there may be added a compound which is decomposed with an acid to generate an acid, that is, acid-propagating compound. For these compounds, reference should be made to J. Photopolym. Sci. and Tech., 8, 43–44, 45–46 (1995), and ibid., 9, 29–30 (1996).

Examples of the acid-propagating compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid-propagating compound-like behavior.

In the resist composition comprising the sulfonyldiazomethane as the photoacid generator according to the invention, an appropriate amount of the acid-propagating compound is up to 2 parts, and especially up to 1 part by weight per 100 parts by weight of the solids in the composition. Excessive amounts of the acid-propagating compound make diffusion control difficult, leading to degradation of resolution and pattern configuration.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl) pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrroidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (D1) may also be included alone or in admixture.

$$N(X')_w(Y)_{3-w} \quad (D1)$$

In the formula, w is equal to 1, 2 or 3; Y is independently hydrogen or a straight, branched or cyclic alkyl group of 1 to 20 carbon atoms which may contain a hydroxyl group or ether structure; and X' is independently selected from groups of the following general formulas (X'1) to (X'3), and two or three X' may bond together to form a ring.

(X'1)

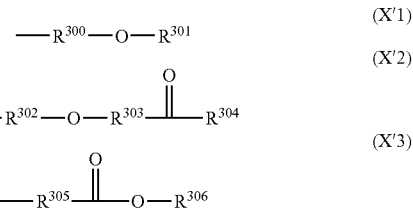

(X'2)

(X'3)

In the formulas, $R^{300}$, $R^{302}$ and $R^{305}$ are independently straight or branched alkylene groups of 1 to 4 carbon atoms; $R^{301}$, $R^{304}$ and $R^{306}$ are independently hydrogen, straight, branched or cyclic alkyl groups of 1 to 20 carbon atoms, which may contain at least one hydroxyl group, ether structure, ester structure or lactone ring; and $R^{303}$ is a single bond or a straight or branched alkylene group of 1 to 4 carbon atoms.

Illustrative examples of the basic compounds of formula (D1) include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy) ethyl}amine, tris{2-(1-ethoxyethoxy)ethyl}amine, tris{2-(1-ethoxypropoxy)ethyl}amine, tris[2-{2-(2- hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more of cyclic structure-bearing basic compounds having the following general formula (D2).

(D2)

Herein X' is as defined above, and $R^{307}$ is a straight or branched alkylene group of 2 to 20 carbon atoms which may contain one or more carbonyl groups, ether structures, ester structures or sulfide structures.

Illustrative examples of the cyclic structure-bearing basic compounds having formula (D2) include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl) methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (D3) to (D6) may be blended.

(D3)

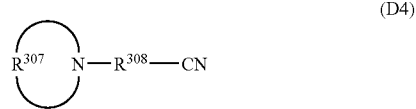

(D4)

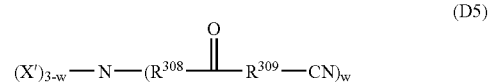

(D5)

-continued

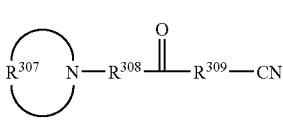
(D6)

Herein, X', $R^{307}$ and w are as defined above, and $R^{308}$ and $R^{309}$ each are independently a straight or branched alkylene group of 1 to 4 carbon atoms.

Illustrative examples of the cyano-bearing basic compounds having formulae (D3) to (D6) include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The basic compounds may be used alone or in admixture of two or more. The basic compound is preferably formulated in an amount of 0 to 2 parts, and especially 0.01 to 1 part by weight, per 100 parts by weight of the solids in the resist composition. The use of more than 2 parts of the basis compound would result in too low a sensitivity.

Component (E)

Illustrative, non-limiting, examples of the organic acid derivatives (E) include phenol, cresol, catechol, resorcinol, pyrogallol, fluoroglycin, bis(4-hydroxyphenyl)methane, 2,2-bis(4'-hydroxyphenyl)propane, bis(4-hydroxyphenyl) sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

In the resist composition comprising the sulfonyldiazomethane as the photoacid generator according to the invention, the organic acid derivative is preferably formulated in an amount of up to 5 parts, and especially up to 1 part by weight, per 100 parts by weight of the solids in the resist composition. The use of more than 5 parts of the organic acid derivative would result in too low a resolution. Depending on the combination of the other components in the resist composition, the organic acid derivative may be omitted.

Component (F)

Component (F) is an organic solvent. Illustrative, non-limiting, examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methylpyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethyl sulfoxide, γ-butyrolactone, propylene glycol methyl ether acetate, propylene glycol ethyl ether acetate, propylene glycol propyl ether acetate, methyl lactate, ethyl lactate, propyl lactate, and tetramethylsulfonic acid. Of these, the propylene glycol alkyl ether acetates and alkyl lactates are especially preferred. The solvents may be used alone or in admixture of two or more. An exemplary useful solvent mixture is a mixture of a propylene glycol alkyl ether acetate and an alkyl lactate. It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture.

When the propylene glycol alkyl ether acetate is used as the solvent, it preferably accounts for at least 50% by weight of the entire solvent. Also when the alkyl lactate is used as the solvent, it preferably accounts for at least 50% by weight of the entire solvent. When a mixture of propylene glycol alkyl ether acetate and alkyl lactate is used as the solvent, that mixture preferably accounts for at least 50% by weight of the entire solvent. In this solvent mixture, it is further preferred that the propylene glycol alkyl ether acetate is 60 to 95% by weight and the alkyl lactate is 40 to 5% by weight. A lower proportion of the propylene glycol alkyl ether acetate would invite a problem of inefficient coating whereas a higher proportion thereof would provide insufficient dissolution and allow for particle and foreign matter formation. A lower proportion of the alkyl lactate would provide insufficient-dissolution and cause the problem of many particles and foreign matter whereas a higher proportion thereof would lead to a composition which has a too high viscosity to apply and loses storage stability.

The solvent is preferably used in an amount of 300 to 2,000 parts by weight, especially 400 to 1,000 parts by weight per 100 parts by weight of the solids in the resist composition. The solvent concentration is not limited thereto as long as a film can be formed by existing methods.

Component (G)

In one preferred embodiment, the resist composition further contains (G) a compound with a molecular weight of up to 3,000 which changes its solubility in an alkaline developer under the action of an acid, that is, a dissolution inhibitor. Typically, a compound obtained by partially or entirely substituting acid labile substituents on a phenol or carboxylic acid derivative having a molecular weight of up to 2,500 is added as the dissolution inhibitor.

Examples of the phenol or carboxylic acid derivative having a molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl)ethane, phenolphthalein, and thymolphthalein. The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)phenyl)methane, 2,2-bis(4'-(2''-tetrahydropyranyloxy))propane, 2,2-bis(4'-(2''-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4'-(1''-ethoxyethoxy)phenyl)propane, 2,2-bis(4'-(1''-ethoxypropyloxy)phenyl)propane, tert-butyl 4,4-bis(4'-(2''-tetrahydropyranyloxy)phenyl)valerate, tert-butyl 4,4-bis(4'-(2''-tetrahydrofuranyloxy)phenyl)valerate, tert-butyl 4,4-bis(4'-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)valerate, tert-butyl 4,4-bis(4'-(1''-ethoxyethoxy)phenyl)valerate, tert-butyl 4,4-bis(4'-(1''-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2''-tetrahydropyranyloxy)phenyl)ethane, 1,1,2-tris(4'-(2''-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, and 1,1,2-tris(4'-(1'-ethoxypropyloxy)phenyl)ethane.

In the resist composition comprising the sulfonyldiazomethane of formula (1) or (1a) as the photoacid generator according to the invention, an appropriate amount of the dissolution inhibitor is up to 20 parts, and especially up to 15 parts by weight per 100 parts by weight of the solids in the resist composition. With more than 20 parts of the dissolution inhibitor, the resist composition becomes less heat resistant because of an increased content of monomer components.

Component (H)

In a chemical amplification, negative working, resist composition as well, the sulfonyldiazomethane of formula (1) or (1a) according to the invention may be used as the photoacid generator. This composition further contains an alkali-soluble resin as component (H), examples of which are intermediates of the above-described component (A) though not limited thereto. Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers.

Alkali-soluble resins comprising units of the following formula (2), (2'), (2") or (2''') are especially preferred.

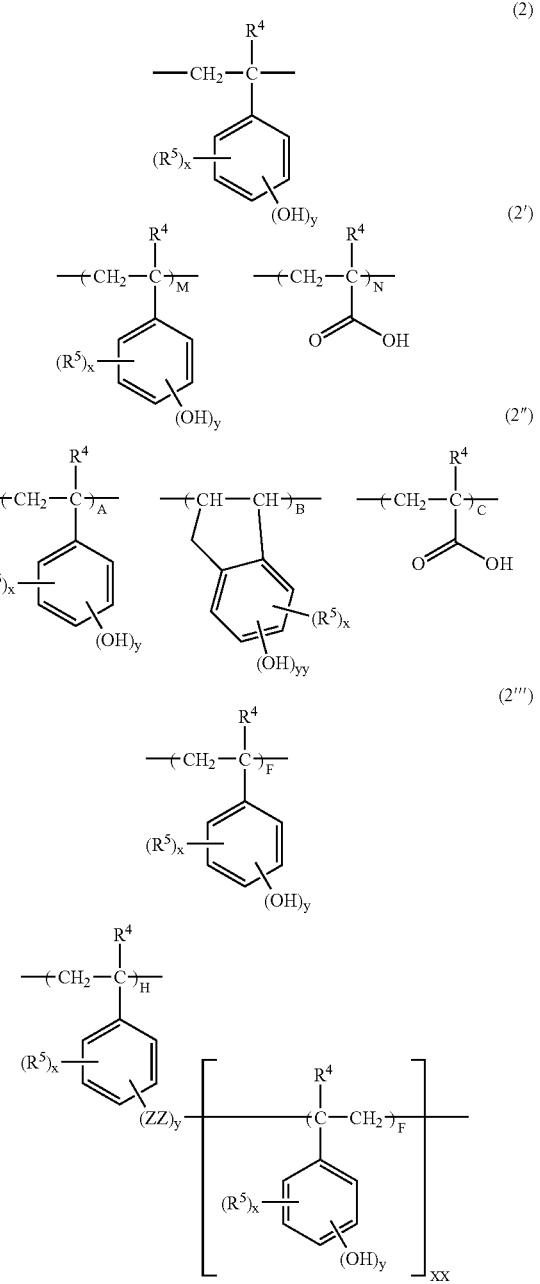

Herein $R^4$ is hydrogen or methyl; and $R^5$ is a straight, branched or cyclic alkyl group of 1 to 8 carbon atoms. The subscript x is 0 or a positive integer; y is a positive integer, satisfying $x+y \leq 5$; yy is 0 or a positive integer, satisfying $x+yy \leq 5$; M and N are positive integers, satisfying $0 < N/(M+N) \leq 0.5$; A and B are positive integers, C is 0 or a positive integer, satisfying $0 < B/(A+B+C) \leq 0.5$, ZZ is a divalent group selected from among $CH_2$, CH(OH), $CR^5$(OH), C=O and $C(OR^5)(OH)$, or a trivalent organic group represented by —C(OH)=; F is independently a positive integer, and H is a positive integer, satisfying $0.001 \leq H/(H+F) \leq 0.1$; and XX is 1 or 2.

The polymer should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

To impart a certain function, suitable substituent groups may be introduced into some of the phenolic hydroxyl and carboxyl groups on the foregoing polymer. Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce acid-decomposable substituent groups such as t-butoxycarbonyl and relatively acid-undecomposable substituent groups such as t-butyl and t-butoxycarbonylmethyl.

In the resist composition, the above resin is blended in any desired amount, preferably of 65 to 99 parts by weight, especially 70 to 98 parts by weight per 100 parts by weight of the solids.

Also contained in the negative resist composition is (I) an acid crosslinking agent capable of forming a crosslinked structure under the action of an acid. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified, negative resist composition comprising the sulfonyldiazomethane. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred acid crosslinking agents are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

An appropriate amount of the acid crosslinking agent is, but not limited thereto, about 1 to 20 parts, and especially about 5 to 15 parts by weight per 100 parts by weight of the solids in the resist composition. The acid crosslinking agents may be used alone or in admixture of any.

Component (J) is an alkali-soluble compound having a molecular weight of up to 2,500. Any suitable compound may be used although a compound having at least two phenol and/or carboxyl groups is preferred. Illustrative, non-limiting, examples of the alkali-soluble compound (J) include cresol, catechol, resorcinol, pyrogallol, fluoroglycin, bis(4-hydroxyphenyl)methane, 2,2-bis(4'-hydroxyphenyl) propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanolic acid, benzoic acid, salicylic acid, 4,4-bis(4'-hydroxyphenyl) valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more. The alkali-soluble compound is blended in any desired amount, preferably of 0 to 20 parts by weight, especially 2 to 10 parts by weight per 100 parts by weight of the solids in the resist composition.

In the chemical amplification type resist composition according to the invention, there may be added such additives as a surfactant for improving coating, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products Co., Ltd.), Megaface F171, F172 and F173 (Dainippon Ink & Chemicals, Inc.), Fluorad FC430 and FC431 (Sumitomo 3M Co., Ltd.), Aashiguard AG710, Surflon S-381, S-382, SC101, SC102, SC103, SC104, SC105, SC106, Surfynol E1004, KH-10, KH-20, KH-30 and KH-40 (Asahi Glass Co., Ltd.), organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo K.K.). Inter alia, FC430, Surflon S-381, Surfynol E1004, KH-20 and KH-30 are preferred. These surfactants may be used alone or in admixture.

In the chemical amplification type resist composition according to the invention, the surfactant is preferably formulated in an amount of up to 2 parts, and especially up to 1 part by weight, per 100 parts by weight of the solids in the resist composition.

In the chemical amplification type resist composition according to the invention, a UV absorber may be added. Those UV absorbers described in JP-A 11-190904 are useful, but the invention is not limited thereto. Exemplary UV absorbers are diaryl sulfoxide derivatives such as bis(4-hydroxyphenyl) sulfoxide, bis(4-tert-butoxyphenyl) sulfoxide, bis(4-tert-butoxycarbonyloxyphenyl) sulfoxide, and bis [4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis [4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazide group-containing compounds such as complete or partial ester compounds between naphthoquinone-1,2-diazide-5-sulfonic acid chloride and 2,3,4-trihydroxybenzophenone and complete or partial ester compounds between naphthoquinone-1,2-diazide-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate. The UV absorber may or may not be added to the resist composition depending on the type of resist composition. An appropriate amount of UV absorber, if added, is 0 to 10 parts, more preferably 0.5 to 10 parts, most preferably 1 to 5 parts by weight per 100 parts by weight of the base resin.

For the microfabrication of integrated circuits, any well-known lithography may be used to form a resist pattern from the chemical amplification type resist composition comprising the sulfonyldiazomethane photoacid generator of formula (1) or (1a) and the resin which changes solubility in an alkaline developer under the action of acid according to the invention.

The composition is applied onto a substrate (e.g., Si, $SiO_2$, SiN, SiON, TiN, WSi, BPSG, SOG, organic anti-reflecting film, etc.) by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 120° C. for 1 to 5 minutes. The resulting resist film is generally 0.1 to 2.0 µm thick. With a mask having a desired pattern placed above the resist film, the resist film is then exposed to actinic radiation, preferably having an exposure wavelength of up to 300 nm, such as UV, deep-UV, electron beams, x-rays, excimer laser light, γ-rays and synchrotron radiation in an exposure dose of about 1 to 200 mJ/cm$^2$, preferably about 10 to 100 mJ/cm$^2$. The film is further baked on a hot plate at 60 to 150° C. for 1 to 5 minutes, preferably 80 to 120° C. for 1 to 3 minutes (post-exposure baking=PEB).

Thereafter the resist film is developed with a developer in the form of an aqueous base solution, for example, 0.1 to 5%, preferably 2 to 3% aqueous solution of tetramethylammonium hydroxide (TMAH) for 0.1 to 3 minutes, preferably 0.5 to 2 minutes by conventional techniques such as dipping, puddling or spraying. In this way, a desired resist pattern is formed on the substrate. It is appreciated that the resist composition of the invention is best suited for micropatterning using such actinic radiation as deep UV with a wavelength of 254 to 193 nm, vacuum UV with a wavelength of 157 nm, electron beams, x-rays, excimer laser light, γ-rays and synchrotron radiation. With any of the above-described parameters outside the above-described range, the process may sometimes fail to produce the desired pattern.

EXAMPLE

Examples of the invention are given below by way of illustration and not by way of limitation.

Synthesis Example 1

Synthesis of 3,4-di(n-hexyloxy)-6-methylthiophenol

In 100 g of ethanol were dissolved 100 g (0.8 mol) of 4-methylcatechol and 71 g (1.77 mol) of sodium hydroxide. To the solution at 70° C., 292 g (1.77 mol) of n-bromohexane was added dropwise. The solution was allowed to ripen for 4 hours and cooled to room temperature, after which 400 g of water was added. The oily phase was separated therefrom and concentrated on a rotary evaporator, yielding 200 g of an oily matter. This was distilled in vacuum (boiling point 160–165° C./0.5 Torr), obtaining 91 g (yield 77%) of 1,2-di(n-hexyloxy)-4-methylbenzene.

Next, 91 g (0.31 mol) of the 1,2-di(n-hexyloxy)-4-methylbenzene was dissolved in 270 g of dichloromethane. While cooling in an ice/water bath, 49.7 g (0.31 mol) of bromine was added dropwise at a temperature below 10° C. After the completion of dropwise addition, 200 g of water was added. The organic layer was separated and washed with a saturated sodium hydrogen carbonate aqueous solution. The organic layer was concentrated on a rotary evaporator, yielding 120 g of an oily matter. This was distilled in vacuum (boiling point 180–190° C./0.5 Torr), obtaining 104 g (yield 90%) of 5-bromo-1,2-di(n-hexyloxy)-4-methylbenzene.

Using 104 g (0.28 mol) of the 5-bromo-1,2-di(n-hexyloxy)-4-methylbenzene, 6.8 g (0.28 mol) of metallic magnesium and 210 g of tetrahydrofuran, a Grignard reagent was prepared in a conventional manner. The Grignard reagent was ice cooled, to which 8.1 g (0.25 mol) of colloidal sulfur was added at a temperature below 20° C. The solution was ripened for 2 hours at room temperature, then ice cooled again. To the solution, 38 g of conc. hydrochloric acid (12N) and 126 g of water were added. The organic layer was separated and concentrated on a rotary evaporator, yielding 94 g of an oily matter. To the oily matter were added 500 g of water, 10 g (0.25 mol) of sodium hydroxide and 50 g of toluene, which were stirred. The aqueous layer was separated. To the aqueous layer were added 45 g of conc. hydrochloric acid (12N) and 200 g of dichloromethane. The organic layer was separated and concentrated on a rotary evaporator, yielding 60 g (yield 66%) of 3,4-di(n-hexyloxy)-6-methylthiophenol.

Synthesis Example 2

Synthesis of bis(3,4-di(n-hexyloxy)-6-methylbenzenesulfonyl)methane

In 120 g of ethanol were dissolved 60 g (0.18 mol) of the above 3,4-di(n-hexyloxy)-6-methylthiophenol and 7.4 g (0.18 mol) of sodium hydroxide. Then 11.7 g (0.14 mol) of dichloromethane was added dropwise at a temperature below 50° C. The solution was heated on an oil bath to 60° C. and allowed to ripen at the temperature for 3 hours. The solution was allowed to cool down to room temperature, after which 120 g of water and 100 g of dichloromethane were added. The organic layer was separated and the solvent was removed by means of a rotary evaporator, yielding 52 g of formaldehyde bis(3,4-di(n-hexyloxy)-6-methylbenzenethio)acetal.

To 208 g of acetonitrile were added 52 g of the formaldehyde bis(3,4-di(n-hexyloxy)-6-methylbenzenethio)acetal and 0.9 g (0.0028 mol) of sodium tungstate. The solution was heated on an oil bath to 65° C. Then 45 g (0.46 mol) of aqueous hydrogen peroxide was added dropwise at a temperature below 70° C. The solution was held at the temperature for 4 hours and then cooled on an ice bath whereupon white crystals precipitated. The crystals were filtered, collecting 25 g (yield 37%) of the end bis(3,4-di(n-hexyloxy)-6-methylbenzenesulfonyl)methane.

Synthesis Example 3

Synthesis of bis(3,4-di(n-hexyloxy)-6-methylbenzenesulfonyl)diazomethane

In 50 g of dichloromethane were dissolved 12.7 g (0.0175 mol) of the above bis(3,4-di(n-hexyloxy)-6-methylbenzenesulfonyl)methane and 3.8 g (0.019 mol) of p-toluenesulfonylazide. The solution was cooled on an ice bath, and 2.66 g (0.0175 mol) of 1,8-diazabicyclo[5.4.0]-7-undecene (DBU) was added at a temperature below 5° C. The solution was allowed to ripen at the temperature for 15 minutes, after which 100 g of water was added. The organic layer was separated and washed with 100 g of water, after which the solvent was removed by means of a rotary evaporator, obtaining 35 g of an oily matter. It was purified by silica gel column chromatography (eluent: dichloromethane), obtaining 9.5 g (yield 72%) of the end compound, bis(3,4-di(n-hexyloxy)-6-methylbenzenesulfonyl)diazomethane.

The thus obtained bis(3,4-di(n-hexyloxy)-6-methyl-benzenesulfonyl)diazomethane was analyzed by nuclear magnetic resonance (NMR) spectroscopy, infrared (IR) absorption spectroscopy and thermogravimetric analysis (Tdec), with the results shown below.

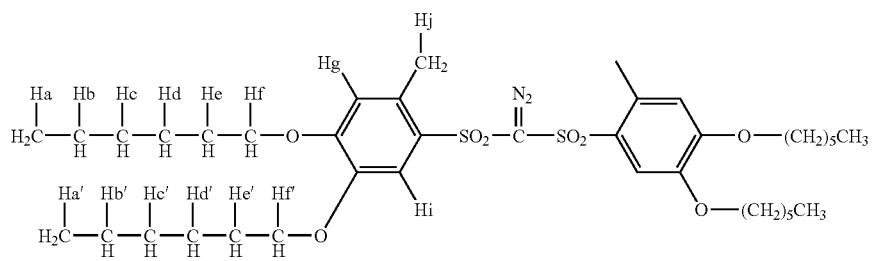

| $^1$H-NMR: CDCl$_3$ (ppm) | | | |
|---|---|---|---|
| (1) Ha, Ha' | 0.880–0.941 | multiplet | 12H |
| (2) Hb, Hb', Hc, Hc' | 1.307–1.405 | multiplet | 8H |
| (3) Hd, Hd' | 1.426–1.506 | multiplet | 8H |
| (4) He, He' | 1.741–1.881 | multiplet | 8H |
| (5) Hf (or Hf') | 3.891–3.941 | triplet | 4H |
| (6) Hf' (or Hf) | 3.947–4.023 | triplet | 4H |
| (7) Hg | 6.591 | singlet | 2H |
| (8) Hi | 7.256 | singlet | 2H |
| (9) Hj | 2.449 | singlet | 6H |
| IR(cm$^{-1}$): | 2956, 2935, 2873, 2862, 2104, 1599, 1568, 1523, 1468, 1389, 1350, 1336, 1319, 1282, 1219, 1144, 1134, 1032, 962, 924, 872, 862, 735, 688, 661, 640, 573, 563, 546, 532 | | |

Thermogravimetric analysis: 130.5° C. (the temperature at which a weight change of −0.1 wt % occurred upon heating at a rate of 10° C./min from room temperature)

Synthesis Example 4

Synthesis of bis(3,4-di(n-butyloxy)-6-methylbenzenesulfonyl)diazomethane

The end compound, bis(3,4-di(n-butyloxy)-6-methylbenzenesulfonyl)diazomethane was synthesized as in Synthesis Examples 1 to 3 except that n-butyl bromide was used instead of n-hexyl bromide in Synthesis Example 1. The results of NMR, IR and thermogravimetric analyses are shown below.

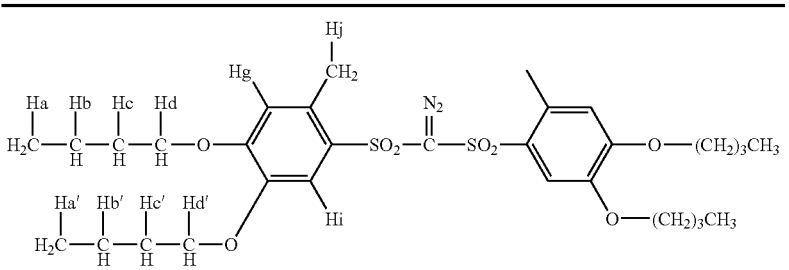

| $^1$H-NMR: CDCl$_3$ (ppm) | | | |
|---|---|---|---|
| (1) Ha, Ha' | 0.955–1.019 | multiplet | 12H |
| (2) Hb, Hb' | 1.426–1.588 | multiplet | 8H |
| (3) Hc, Hc' | 1.733–1.863 | multiplet | 8H |
| (4) Hd (or Hd') | 3.906–3.949 | multiplet | 4H |
| (5) Hd' (or Hd) | 3.986–4.030 | triplet | 4H |
| (6) Hg | 6.599 | singlet | 2H |
| (7) Hi | 7.264 | singlet | 2H |
| (8) Hj | 2.449 | singlet | 6H |

| IR(cm$^{-1}$): | 2958, 2935, 2873, 2104, 1599, 1568, 1522, 1468, 1390, 1348, 1336, 1319, 1281, 1219, 1144, 1134, 1068, 1038, 964, 867, 852, 688, 607, 571, 563, 542, 528 |
|---|---|

Thermogravimetric analysis: 124.2° C. (the temperature at which a weight change of −0.1 wt % occurred upon heating at a rate of 10° C./min from room temperature)

Synthesis Example 5

Synthesis of bis(2,4-di(n-butyloxy)benzenesulfonyl)diazomethane

The end compound, bis(2,4-di(n-butyloxy)benzenesulfonyl)diazomethane was synthesized as in Synthesis Example 4 except that resorcinol was used instead of 4-methylcatechol in Synthesis Example 4. The results of NMR, IR and thermogravimetric analyses are shown below.

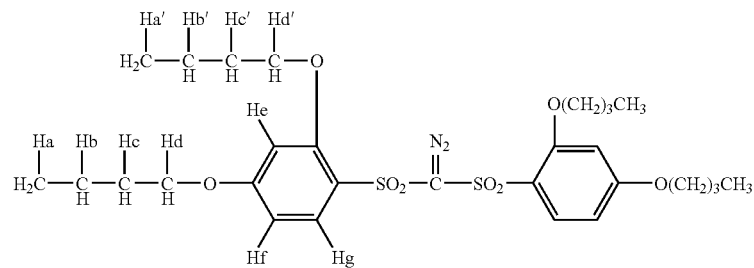

$^1$H-NMR: CDCl$_3$ (ppm)

| (1) Ha, Ha' | 0.959–1.008 | triplet | 12H |
|---|---|---|---|
| (2) Hb, Hb' | 1.428–1.571 | multiplet | 8H |
| (3) Hc, Hc' | 1.723–1.892 | multiplet | 8H |
| (4) Hd (or Hd') | 3.954–3.997 | multiplet | 4H |
| (5) Hd' (or Hd) | 4.010–4.054 | triplet | 4H |
| (6) He, Hf | 6.373–6.445 | multiplet | 4H |
| (7) Hg | 7.651–7.680 | doublet | 2H |

| IR(cm$^{-1}$): | 2959, 2935, 2873, 2121, 1603, 1576, 1495, 1471, 1433, 1402, 1352, 1344, 1333, 1290, 1265, 1230, 1203, 1163, 1142, 1130, 1070, 1031, 1022, 1011, 978, 835, 734, 706, 650, 638, 584, 573, 552, 536 |
|---|---|

Thermogravimetric analysis: 144.5° C. (the temperature at which a weight change of −0.1 wt % occurred upon heating at a rate of 10° C./min from room temperature)

Synthesis Example 6

Synthesis of bis(2,5-di(n-butyloxy)benzenesulfonyl)diazomethane

The end compound, bis(2,5-di(n-butyloxy)benzenesulfonyl)diazomethane was synthesized as in Synthesis Example 4 except that hydroquinone was used instead of 4-methylcatechol in Synthesis Example 4. The results of NMR, IR and thermogravimetric analyses are shown below.

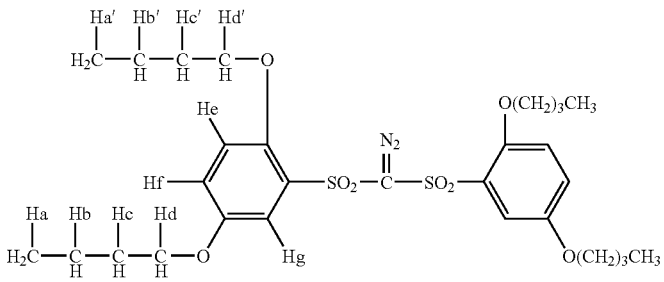

$^1$H-NMR: CDCl$_3$ (ppm)

| | | | | |
|---|---|---|---|---|
| (1) Ha, Ha' | 0.949–0.998 | triplet | 12H | |
| (2) Hb, Hb' | 1.409–1.569 | multiplet | 8H | |
| (3) Hc, Hc' | 1.683–1.861 | multiplet | 8H | |
| (4) Hd (or Ha') | 3.840–3.883 | multiplet | 4H | |
| (5) Hd' (or Hd) | 3.954–4.000 | triplet | 4H | |
| (6) He | 6.770–6.800 | doublet | 2H | |
| (7) Hf | 6.970–7.010 | quadrulet | 2H | |
| (8) Hg | 7.218–7.228 | doublet | 2H | |

IR(cm$^{-1}$): 2958, 2933, 2873, 2133, 1578, 1498, 1470, 1416, 1400, 1390, 1379, 1346, 1331, 1317, 1282, 1228, 1217, 1207, 1163, 1142, 1066, 1053, 1038, 1028, 997, 982, 968, 895, 874, 841, 835, 814, 804, 719, 700, 646, 598, 580, 532

Thermogravimetric analysis: 144.8° C. (the temperature at which a weight change of −0.1 wt % occurred upon heating at a rate of 10° C./min from room temperature)

Reference Synthesis Example 1

Synthesis of bis(2,4-dimethoxybenzenesulfonyl)methane

Using 100 g (0.46 mol) of 4-bromo-1,3-dimethoxybenzene, 11.2 g (0.46 mol) of metallic magnesium and 290 g of tetrahydrofuran, a Grignard reagent was prepared in a conventional manner. The Grignard reagent was ice cooled, to which 14.7 g (0.46 mol) of colloidal sulfur was added at a temperature below 20° C. The solution was allowed to ripen for 2 hours at room temperature, then ice cooled again. To the solution, 62 g of conc. hydrochloric acid (12N) and 200 g of water were added. The organic layer was concentrated on a rotary evaporator, yielding 84 g of an oily matter. Then 84 g of the oily matter was dissolved in 250 g of ethanol and 29.3 g (0.345 mol) of dichloromethane. 18.4 g (0.46 mol) of sodium hydroxide was added to the solution, which was warmed on a hot water bath at 50° C. for 2 hours. Then 200 g of water and 200 g of dichloromethane were added. The organic layer was separated therefrom and concentrated on a rotary evaporator, yielding 80 g of an oily matter.

To 80 g of the concentrate were added 400 g of ethanol and 3.8 g (0.01 mol) of sodium tungstate. The solution was heated at 70° C., after which 150 g (1.45 mol) of 35% aqueous hydrogen peroxide was added dropwise over 2 hours. The solution was allowed to ripen at the temperature for 4 hours and then allowed to cool down whereupon white crystals precipitated out. Filtration and drying yielded 68 g of the end compound (yield 71%).

Reference Synthesis Example 2

Synthesis of bis(2,4-dimethoxybenzenesulfonyl)diazomethane

In 200 g of dichloromethane, 20 g (0.048 mol) of the above bis(2,4-dimethoxybenzenesulfonyl)methane was dissolved, and 11.4 g (0.058 mol) of p-toluenesulfonylazide added. At room temperature, 7.3 g (0.048 mol) of 1,8-diazabicyclo-[5.4.0]-7-undecene (DBU) was added. The solution was allowed to ripen at the temperature for 60 minutes, after which 100 g of water and 16 g of conc. hydrochloric acid were added. The organic layer was separated and washed with 100 g of water. The crystals precipitated were removed from the organic layer, which was concentrated on a rotary evaporator, obtaining an oily matter. It was purified by silica gel column chromatography (eluent: dichloromethane), obtaining 3.2 g (yield 15%) of the end compound, bis(2,4-dimethoxybenzenesulfonyl)diazomethane. The synthesis of the end compound was confirmed by NMR and IR analyses However, this compound, bis(2,4-dimethoxybenzenesulfonyl)diazomethane was substantially insoluble in typical resist solvents such as propylene glycol methyl ether acetate and ethyl lactate as demonstrated by a solubility of less than 0.5 wt %. Thus this compound could not be examined for resist performance.

Examples 1–24 and Comparative Examples 1–3

Resist materials were formulated in accordance with the formulation shown in Tables 1 to 3. The components used are shown below.

Polymer A: poly(p-hydroxystyrene) in which hydroxyl groups are protected with 15 mol % of 1-ethoxyethyl groups and 15 mol % of tert-butoxycarbonyl groups, having a weight average molecular weight of 12,000.

Polymer B: poly(p-hydroxystyrene) in which hydroxyl groups are protected with 30 mol % of 1-ethoxyethyl groups, having a weight average molecular weight of 12,000.

Polymer C: poly(p-hydroxystyrene) in which hydroxyl groups are protected with 25 mol % of 1-ethoxyethyl groups and crosslinked with 3 mol % of 1,2-propanediol divinyl ether, having a weight average molecular weight of 13,000.

Polymer D: poly(p-hydroxystyrene) in which hydroxyl groups are protected with 28 mol % of tert-pentyl groups, having a weight average molecular weight of 8,000.

Polymer E: p-hydroxystyrene/2-ethyl-2-adamantyl acrylate copolymer having a compositional ratio (molar ratio) of 70:30 and a weight average molecular weight of 15,000.

Polymer F: p-hydroxystyrene/1-ethyl-1-norbornene methacrylate copolymer having a compositional ratio (molar ratio) of 70:30 and a weight average molecular weight of 15,000.

Polymer G: p-hydroxystyrene/tert-butyl acrylate copolymer having a compositional ratio (molar ratio) of 65:35 and a weight average molecular weight of 15,000.

Polymer H: p-hydroxystyrene/1-ethylcyclopentyl methacrylate copolymer having a compositional ratio (molar ratio) of 65:35 and a weight average molecular weight of 15,000.

Polymer I: p-hydroxystyrene/1-ethylcyclopentyl methacrylate/p-tert-pentyloxystyrene copolymer having a compositional ratio (molar ratio) of 70:8:22 and a weight average molecular weight of 16,000.

Polymer J: p-hydroxystyrene/1-ethylcyclopentyl methacrylate/styrene copolymer having a compositional ratio (molar ratio) of 65:10:25 and a weight average molecular weight of 12,000.

Polymer K: p-hydroxystyrene/indene copolymer having a compositional ratio (molar ratio) of 80:20 in which hydroxyl groups on the hydroxystyrene are protected with 20 mol % of tert-butoxycarbonyl groups, and having a weight average molecular weight of 10,000.

Polymer L: p-hydroxystyrene/indene/2-ethyl-2-adamantyl methacrylate copolymer having a compositional ratio (molar ratio) of 82:4:14 and a weight average molecular weight of 8,000.

Polymer M: p-hydroxystyrene/indene/1-ethyl-1-norbornene methacrylate copolymer having a compositional ratio (molar ratio) of 84:4:12 and a weight average molecular weight of 8,000.

Polymer N: poly(p-hydroxystyrene) in which hydroxyl groups are protected with 8 mol % of acetyl groups, having a weight average molecular weight of 8,000.

PAG1: compound of Synthesis Example 3
PAG2: compound of Synthesis Example 4
PAG3: compound of Synthesis Example 5
PAG4: compound of Synthesis Example 6
PAG5: (4-tert-butoxyphenyl)diphenylsulfonium 10-camphorsulfonate
PAG6: bis(4-methoxyphenylsulfonyl)diazomethane
PAG7: bis(cyclohexylsulfonyl)diazomethane
PAG8: bis(4-methylphenylsulfonyl)diazomethane
PAG9: N-10-camphorsulfonyloxysuccinimide
Crosslinker A: 1,3,5,7-tetramethoxymethylglycoluril
Dissolution inhibitor: bis(4-(2'-tetrahydropyranyloxy)phenyl)methane
Basic compound A: tri(n-butyl)amine
Basic compound B: tris(2-methoxyethyl)amine
Organic acid derivative A: 4,4-bis(4'-hydroxyphenyl)valeric acid
Organic acid derivative B: salicylic acid
Surfactant A: FC-430 (Sumitomo 3M Co., Ltd.)
Surfactant B: Surflon S-381 (Asahi Glass Co., Ltd.)
UV absorber: 9,10-dimethylanthracene
Solvent A: propylene glycol methyl ether acetate
Solvent B: ethyl lactate The resist materials thus obtained were each filtered through a 0.2-μm Teflon® filter, thereby giving resist solutions. These resist solutions were spin-coated onto silicon wafers having an organic antireflection film (DUV-44, Brewer Science) of 800 Å thick coated thereon, so as to give a dry thickness of 0.6 μm.

The coated wafer was then baked on a hot plate at 100° C. for 90 seconds. The resist films were exposed to ⅔ annular illumination using an excimer laser stepper NSR-S202A (Nikon Corporation, NA=0.6), then baked (PEB) at 110° C. for 90 seconds, and developed with a solution of 2.38% tetramethylammonium hydroxide in water, thereby giving positive patterns (Examples 1 to 23 and Comparative Examples 1–3) or negative pattern (Example 24).

The resulting resist patterns were evaluated as described below.

Resist Pattern Evaluation

The optimum exposure dose (sensitivity Eop) was the exposure dose which provided a 1:1 resolution at the top and bottom of a 0.18-μm line-and-space pattern. The minimum line width (μm) of a line-and-space pattern which was ascertained separate at this dose was the resolution of a test resist. The shape in cross section of the resolved resist pattern was examined under a scanning electron microscope. The depth of focus (DOF) was determined by offsetting the focal point and judging the resist to be satisfactory when the resist pattern shape was kept rectangular and the resist pattern film thickness was kept above 80% of that at accurate focusing.

The PED stability of a resist was evaluated by effecting post-exposure bake (PEB) after 24 hours of holding from exposure at the optimum dose and determining a variation in line width. The less the variation, the greater is the PED stability.

The results of resist pattern evaluation are shown in Table 4.

Other Evaluation

The solubility of resist material in a solvent mixture was examined by visual observation and in terms of clogging upon filtration.

With respect to the applicability of a resist solution, uneven coating was visually observed. Additionally, using an optical interference film gage Lambda-Ace VM-3010 (Dainippon Screen Mfg. Co., Ltd.), the thickness of a resist film on a common wafer was measured at different positions, based on which a variation from the desired coating thickness (0.6 µm) was calculated. The applicability was rated "good" when the variation was within 0.5% (that is, within 0.003 µm), "unacceptable" when the variation was within 1%, and "poor" when the variation was more than 1%.

Storage stability was judged in terms of foreign matter precipitation or sensitivity change with the passage of time. After the resist solution was aged for 100 days at the longest, the number of particles of 0.3 µm or larger per ml of the resist solution was counted by means of a particle counter KL-20A (Rion Co., Ltd.). Also, a change with time of sensitivity (Eop) from that immediately after preparation was determined. The storage stability was rated "good" when the number of particles is not more than 5 or when the sensitivity change was within 5%, and "poor" otherwise.

Debris appearing on the developed pattern was observed under a scanning electron microscope (TDSEM) model S-7280H (Hitachi Ltd.). The resist film was rated "good" when the number of foreign particles was up to 10 per 100 µm$^2$, "unacceptable" when from 11 to 15, and "poor" when more than 15.

Debris left after resist peeling was examined using a surface scanner Surf-Scan 6220 (Tencol Instruments). A resist-coated 8-inch wafer was subjected to entire exposure rather than patterned exposure, processed in a conventional manner, and developed with a 2.38% TMAH solution before the resist film was peeled off (only the resist film in the exposed area was peeled). After the resist film was peeled, the wafer was examined and rated "good" when the number of foreign particles of greater than 0.20 µm was up to 100, "unacceptable" when from 101 to 150, and "poor" when more than 150.

The results are shown in Table 5.

TABLE 1

| Composition (pbw) | Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Polymer A | 80 | | | | | | | | | | | 40 |
| Polymer B | | 80 | | | | | | | | | | |
| Polymer C | | | 80 | | | | | | | | | |
| Polymer D | | | | 80 | | | | | | | | |
| Polymer E | | | | | 80 | | | | | | | |
| Polymer F | | | | | | 80 | | | | | | |
| Polymer G | | | | | | | 80 | | | | | |
| Polymer H | | | | | | | | 80 | | | | |
| Polymer I | | | | | | | | | 80 | | | |
| Polymer J | | | | | | | | | | 80 | | |
| Polymer K | | | | | | | | | | | 80 | |
| Polymer L | | | | | | | | | | | | 80 |
| Polymer M | | | | | | | | | | | | |
| Polymer N | | | | | | | | | | | | |
| PAG1 | | | 2 | 2 | 2 | | | | | | | |
| PAG2 | | | | | | 2 | | | | 2 | | 2 |
| PAG3 | 2 | | 2 | | | | 2 | | | 3.5 | | |
| PAG4 | | 2 | | | | | | 2 | | | 2 | |
| PAG5 | | 1 | | | 1 | | 1 | 1 | | | 2 | |
| PAG6 | | | | | | | | | | | | |
| PAG7 | | | 1 | | | 1 | 1 | | | 2 | | |
| PAG8 | | | | | | | | | | | 1 | |
| PAG9 | | 1 | | | | | | | | | | |
| Dissolution inhibitor | | | | | | | | | | | | |
| Basic compound A | 0.3 | 0.3 | 0.3 | 0.3 | 0.3 | 0.15 | | | | | 0.3 | 0.3 |
| Basic compound B | | | | | | 0.15 | 0.3 | 0.3 | 0.3 | 0.3 | | |
| Organic acid derivative A | | | | | 0.5 | | | | | 0.5 | 0.5 | |
| Organic acid derivative B | | | | | | | 0.5 | | | | | |

TABLE 1-continued

| Composition (pbw) | Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Surfactant A | 0.25 | 0.25 | 0.25 | | | | | | 0.25 | 0.25 | 0.25 | |
| Surfactant B | | | | 0.25 | 0.25 | 0.25 | 0.25 | 0.25 | | | | 0.25 |
| UV absorber | | | | | | | | | | | | |
| Solvent A | 385 | 385 | 385 | 385 | 385 | 385 | 385 | 280 | 382 | 385 | 280 | 385 |
| Solvent B | | | | | | | | 105 | | | 105 | |

TABLE 2

| Composition (pbw) | Example | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| Polymer A | | | 40 | | 60 | | | | | | | |
| Polymer B | | | | | | | | 60 | | | 75 | |
| Polymer C | | | | | | 40 | | | 40 | | | |
| Polymer D | | 70 | 40 | 60 | | 40 | | | | | | |
| Polymer E | | | | | | | 40 | | | 10 | | |
| Polymer F | | | | | | | | | | | | |
| Polymer G | | | | | | | 40 | | | | | |
| Polymer H | | | | | | | | | | | | |
| Polymer I | | 10 | | | | | | 20 | | | | |
| Polymer J | | | | | | | | | | | | |
| Polymer K | | | | | | | | | 40 | | | |
| Polymer L | 40 | | | | 20 | | | | | 70 | | |
| Polymer M | 40 | | | 20 | | | | | | | | |
| Polymer N | | | | | | | | | | | | 80 |
| PAG1 | | | | | 2 | | | 2 | | | | |
| PAG2 | | | 2 | 2 | | | | | | 2 | | |
| PAG3 | 1 | | | | | 2 | 2 | | 2 | | 2 | 2 |
| PAG4 | | 2 | 2 | | | | | | 2 | 2 | | |
| PAG5 | 1 | | | | 1 | | | 2 | | | | 1 |
| PAG6 | | | | 0.5 | | | | 0.5 | | | | |
| PAG7 | | 1.5 | | | | 1.5 | | 1 | 1 | | | 1 |
| PAG8 | | | | | | 0.5 | | | | | | |
| PAG9 | | | 1 | | | 1 | 1 | | | | | |
| Crosslinker A | | | | | | | | | | | | 20 |
| Dissolution inhibitor | | | | | | | | | | | 5 | |
| Basic compound A | | 0.15 | | | 0.3 | 0.3 | | | | 0.3 | | |
| Basic compound B | 0.3 | 0.15 | 0.3 | 0.3 | | | 0.3 | 0.3 | 0.3 | | 0.3 | 0.3 |
| Organic acid derivative A | 0.5 | | | | | | 0.5 | | | | | |
| Organic acid derivative B | | | | 0.25 | | | | | | | | |
| Surfactant A | 0.25 | 0.25 | | | | | | 0.25 | 0.25 | 0.25 | 0.25 | |
| Surfactant B | | | 0.25 | 0.25 | | 0.25 | 0.25 | | | | | 0.25 |
| UV absorber | 0.5 | | | | | | | | | | | |
| Solvent A | 280 | 385 | 385 | 385 | 280 | 385 | 385 | 385 | 280 | 385 | 280 | 385 |
| Solvent B | 105 | | | | 105 | | | | 105 | | 105 | |

TABLE 3

| Composition (pbw) | Comparative Example | | |
|---|---|---|---|
| | 1 | 2 | 3 |
| Polymer A | 80 | | 40 |
| Polymer E | | 80 | |
| Polymer K | | | 40 |
| PAG5 | | | |
| PAG6 | | 2.5 | |
| PAG7 | | | 1 |
| PAG8 | 2.5 | | 2.5 |
| PAG9 | 1 | | |
| Dissolution inhibitor | | | |
| Basic compound A | 0.125 | | |
| Basic compound B | | 0.125 | 0.125 |
| Organic acid derivative A | | | 0.5 |
| Organic acid derivative B | | | |
| Surfactant A | 0.25 | 0.25 | |
| Surfactant B | | 0 | 0.25 |
| UV absorber | | | |
| Solvent A | 385 | 385 | 385 |
| Solvent B | | | |

TABLE 4

|  | Sensitivity (mJ/cm²) | Resolution (μm) | profile | DOF at 0.18 μm (μm) | Off-focus profile* | 24 hr PED dimensional stability (nm) |
|---|---|---|---|---|---|---|
| Example 1 | 37 | 0.14 | rectangular | 1.0 | rectangular | −8 |
| Example 2 | 32 | 0.14 | rectangular | 1.0 | rectangular | −8 |
| Example 3 | 35 | 0.14 | rectangular | 1.0 | rectangular | −10 |
| Example 4 | 34 | 0.14 | rectangular | 1.0 | rectangular | −8 |
| Example 5 | 42 | 0.16 | rectangular | 1.1 | rectangular | −8 |
| Example 6 | 40 | 0.15 | rectangular | 1.0 | rectangular | −10 |
| Example 7 | 38 | 0.14 | rectangular | 1.1 | rectangular | −10 |
| Example 8 | 42 | 0.16 | rectangular | 1.1 | rectangular | −10 |
| Example 9 | 35 | 0.14 | rectangular | 1.1 | rectangular | −8 |
| Example 10 | 41 | 0.15 | rectangular | 1.1 | rectangular | −8 |
| Example 11 | 44 | 0.16 | rectangular | 1.0 | rectangular | 8 |
| Example 12 | 40 | 0.15 | rectangular | 1.1 | rectangular | −8 |
| Example 13 | 38 | 0.15 | rectangular | 1.0 | rectangular | −10 |
| Example 14 | 34 | 0.14 | rectangular | 1.1 | rectangular | −9 |
| Example 15 | 36 | 0.14 | rectangular | 1.1 | rectangular | −10 |
| Example 16 | 35 | 0.15 | rectangular | 1.0 | rectangular | 10 |
| Example 17 | 38 | 0.14 | rectangular | 1.1 | rectangular | −8 |
| Example 18 | 36 | 0.14 | rectangular | 1.0 | rectangular | −10 |
| Example 19 | 42 | 0.15 | rectangular | 0.8 | rectangular | −8 |
| Example 20 | 34 | 0.14 | rectangular | 1.0 | rectangular | −10 |
| Example 21 | 38 | 0.15 | rectangular | 1.0 | rectangular | −10 |
| Example 22 | 42 | 0.14 | rectangular | 1.0 | rectangular | −10 |
| Example 23 | 34 | 0.14 | rectangular | 1.1 | rectangular | −8 |
| Example 24 | 48 | 0.18 | rectangular | 0.8 | rectangular | −8 |
| Comparative Example 1 | 25 | 0.15 | forward taper | 0.8 | forward taper | −10 |
| Comparative Example 2 | 32 | 0.15 | rounded head | 0.8 | rounded head | −8 |
| Comparative Example 3 | 35 | 0.15 | forward taper | 0.8 | forward taper | −10 |

*the shape of a pattern obtained when the focus was shifted −0.4 μm to minus side upon DOF measurement at 0.18 μm

TABLE 5

|  | Dissolution | Application | 100 day storage stability | Debris after development | Debris after resist peeling |
|---|---|---|---|---|---|
| Example 1 | good | good | good | good | good |
| Example 2 | good | good | good | good | good |
| Example 3 | good | good | good | good | good |
| Example 4 | good | good | good | good | good |
| Example 5 | good | good | good | good | good |
| Example 6 | good | good | good | good | good |
| Example 7 | good | good | good | good | good |
| Example 8 | good | good | good | good | good |
| Example 9 | good | good | good | good | good |
| Example 10 | good | good | good | good | good |
| Example 11 | good | good | good | good | good |
| Example 12 | good | good | good | good | good |
| Example 13 | good | good | good | good | good |
| Example 14 | good | good | good | good | good |
| Example 15 | good | good | good | good | good |
| Example 16 | good | good | good | good | good |
| Example 17 | good | good | good | good | good |
| Example 18 | good | good | good | good | good |
| Example 19 | good | good | good | good | good |
| Example 20 | good | good | good | good | good |
| Example 21 | good | good | good | good | good |
| Example 22 | good | good | good | good | good |
| Example 23 | good | good | good | good | good |
| Example 24 | good | good | good | good | good |
| Comparative Example 1 | good | good | <30 days (sensitivity changed) | poor | unacceptable |
| Comparative Example 2 | good | good | good | unacceptable | poor |
| Comparative Example 3 | good | good | good | poor | poor |

Examples 25–29 & Comparative Examples 4–6

Another experiment was performed by preparing resist solutions according to the formulation shown in Table 6 and baking resist coatings under different conditions.

The resist materials were filtered through a 0.2-μm Teflon® filter, thereby giving resist solutions. The resist solutions were spin-coated onto silicon wafers having an organic antireflection film (DUV-44, Brewer Science) of 800 Å thick coated thereon, so as to give a dry thickness of 0.6 μm.

The coated wafers were then baked on a hot plate at 120° C. for 90 seconds. The resist films were exposed to ⅔ annular illumination using an excimer laser stepper NSR-S202A (Nikon Corporation, NA=0.6), then baked (PEB) at 130° C. for 90 seconds, and developed with a solution of 2.38% tetramethylammonium hydroxide in water. It was examined whether or not a pattern was formed. The results are shown in Table 7.

There have been described chemically amplified resist compositions comprising a specific sulfonyldiazomethane containing long-chain alkoxyl groups as the photoacid generator. The compositions have many advantages including improved resolution, improved focus latitude, minimized line width variation or shape degradation even on long-term PED, minimized debris left after coating, development and peeling, and improved pattern profile after development. Because of high resolution, the compositions are suited for microfabrication, especially by deep UV lithography.

Japanese Patent Application No. 2003-035055 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

TABLE 6

| Composition (pbw) | Example | | | | | Comparative Example | | |
|---|---|---|---|---|---|---|---|---|
| | 25 | 26 | 27 | 28 | 29 | 4 | 5 | 6 |
| Polymer F | 80 | | | | | | | |
| Polymer H | | 40 | 80 | | | 80 | 80 | 80 |
| Polymer I | | 40 | | 80 | 40 | | | |
| Polymer J | | | | | 40 | | | |
| PAG3 | 3 | 2 | | 3 | 3 | | | |
| PAG4 | | | 3 | | | | | |
| PAG6 | | | | | | 2 | | 2 |
| PAG7 | | | | | | | | 2 |
| PAG8 | | | | | | | 2 | |
| Dissolution inhibitor | | | | | | | | |
| Basic compound A | 0.3 | 0.3 | 0.3 | 0.3 | 0.3 | 0.3 | 0.3 | 0.3 |
| Basic compound B | | | | | | | | |
| Organic acid derivative A | | | | | 0.5 | | | |
| Organic acid derivative B | | | | | | | | |
| Surfactant A | 0.25 | 0.25 | 0.25 | | | | | |
| Surfactant B | | | | 0.25 | 0.25 | | | |
| UV absorber | | | | | | | | |
| Solvent A | 385 | 385 | 385 | 385 | 385 | 385 | 385 | 385 |
| Solvent B | | | | | | | | |

TABLE 7

| | Sensitivity (mJ/cm²) | Resolution (μm) | Profile |
|---|---|---|---|
| Example 25 | 22 | 0.14 | rectangular |
| Example 26 | 22 | 0.14 | rectangular |
| Example 27 | 24 | 0.16 | rectangular |
| Example 28 | 25 | 0.14 | rectangular |
| Example 29 | 23 | 0.14 | rectangular |
| Comparative Example 4 | 19** | 0.20** | rounded head |
| Comparative Example 5 | 17** | 0.20** | rounded head |
| Comparative Example 6 | 18** | 0.20** | rounded head |

**0.18 μm unresolved; a sensitivity capable of resolving 0.20 μm being reported

The invention claimed is:

1. A sulfonyldiazomethane compound having the following general formula (1):

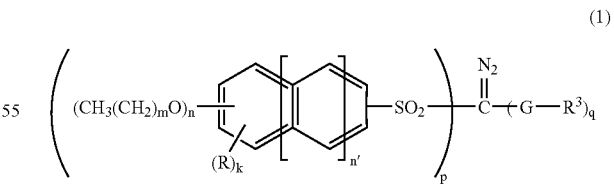

wherein R is independently hydrogen or a substituted or unsubstituted straight, branched or cyclic alkyl or alkoxy group of 1 to 4 carbon atoms, G is $SO_2$ or CO, $R^3$ is a substituted or unsubstituted straight, branched or cyclic alkyl group of 1 to 10 carbon atoms or a substituted or unsubstituted aryl group of 6 to 14 carbon atoms, p is 1 or 2, q is 0 or 1, satisfying p+q=2, n is 2 or 3, n' is 0 or 1, m is independently an integer of 3 to 11, and k is an integer of 0 to 4.

2. A sulfonyldiazomethane compound having the following general formula (1a):

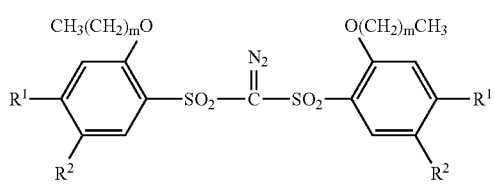

(1a)

wherein $R^1$ and $R^2$ are each independently R or $CH_3(CH_2)_mO$, excluding the combination that both $R^1$ and $R^2$ are R at the same time, R is hydrogen or a substituted or unsubstituted straight, branched or cyclic alkyl or alkoxy group of 1 to 4 carbon atoms, and m is an integer of 3 to 11.

3. A photoacid generator for a chemical amplification type resist composition comprising the sulfonyldiazomethane compound of claim 1.

4. A chemical amplification type resist composition comprising
(A) a resin which changes its solubility in an alkaline developer under the action of an acid, and
(B) the sulfonyldiazomethane compound of claim 1 which generates an acid upon exposure to radiation.

5. A chemical amplification type resist composition comprising
(A) a resin which changes its solubility in an alkaline developer under the action of an acid,
(B) the sulfonyldiazomethane compound of claim 1 which generates an acid upon exposure to radiation, and
(C) a compound capable of generating an acid upon exposure to radiation, other than component (B).

6. The resist composition of claim 4 wherein the resin (A) has such substituent groups having C—O—C linkages that the solubility in an alkaline developer changes as a result of scission of the C—O—C linkages under the action of an acid.

7. The resist composition of claim 6 wherein the resin (A) is a polymer containing phenolic hydroxyl groups in which hydrogen atoms of the phenolic hydroxyl groups are substituted with acid labile groups of one or more types in a proportion of more than 0 mol % to 80 mol % on the average of the entire hydrogen atoms of the phenolic hydroxyl groups, the polymer having a weight average molecular weight of 3,000 to 100,000.

8. The resist composition of claim 7 wherein the resin (A) is a polymer comprising recurring units of the following general formula (2a):

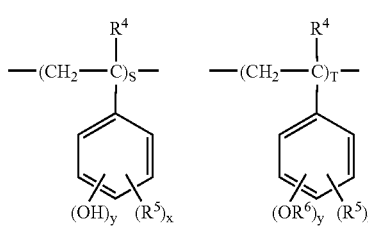

(2a)

wherein $R^4$ is hydrogen or methyl, $R^5$ is a straight, branched or cyclic alkyl group of 1 to 8 carbon atoms, x is 0 or a positive integer, y is a positive integer, satisfying $x+y \leq 5$, $R^6$ is an acid labile group, S and T are positive integers, satisfying $0<T/(S+T)\leq 0.8$,
wherein the polymer contains units in which hydrogen atoms of phenolic hydroxyl groups are partially substituted with acid labile groups of one or more types, a proportion of the acid labile group-bearing units is on the average from more than 0 mol % to 80 mol % based on the entire polymer, and the polymer has a weight average molecular weight of 3,000 to 100,000.

9. The resist composition of claim 6 wherein the resin (A) is a polymer comprising recurring units of the following general formula (2a'):

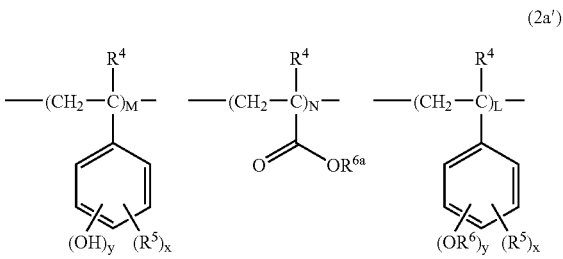

(2a')

wherein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, at least some of $R^{6a}$ being acid labile groups, x is 0 or a positive integer, y is a positive integer, satisfying $x+y\leq 5$, M and N are positive integers, L is 0 or a positive integer, satisfying $0<N/(M+N+L)\leq 0.5$ and $0<(N+L)/(M+N+L)\leq 0.8$,
wherein the polymer contains on the average from more than 0 mol % to 50 mol % of those units derived from acrylate and methacrylate, and also contains on the average from more than 0 mol % to 80 mol % of acid labile group-bearing units, based on the entire polymer, and the polymer has a weight average molecular weight of 3,000 to 100,000.

10. The resist composition of claim 6 wherein the resin (A) is a polymer comprising recurring units of the following general formula (2a''):

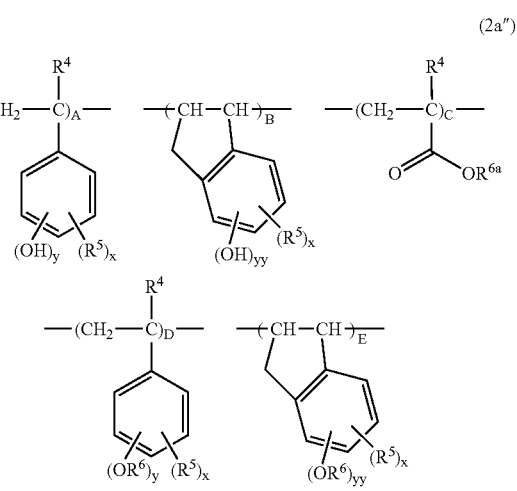

(2a'')

wherein $R^4$ is hydrogen or methyl, $R^5$ is a straight, branched or cyclic alkyl group of 1 to 8 carbon atoms, $R^6$ is an acid labile group, $R^{6a}$ is hydrogen or an acid labile group, at least some of $R^{6a}$ being acid labile groups, x is 0 or a positive integer, y is a positive integer, satisfying x+y≦5, yy is 0 or a positive integer, satisfying x+yy≦5, A and B are positive integers, C, D and E each are 0 or a positive integer, satisfying 0<(B+E)/(A+B+C+D+E)≦0.5 and 0<(C+D+E)/(A+B+C+D+E)≦0.8, wherein the polymer contains on the average from more than 0 mol % to 50 mol % of those units derived from indene and/or substituted indene, and also contains on the average from more than 0 mol % to 80 mol % of acid labile group-bearing units, based on the entire polymer, and the polymer has a weight average molecular weight of 3,000 to 100,000.

11. The resist composition of claims 7 wherein the acid labile group is selected from the class consisting of groups of the following general formulae (4) to (7), tertiary alkyl groups of 4 to 20 carbon atoms, trialkylsilyl groups whose alkyl moieties each have 1 to 6 carbon atoms, oxoalkyl groups of 4 to 20 carbon atoms, and aryl-substituted alkyl groups of 7 to 20 carbon atoms,

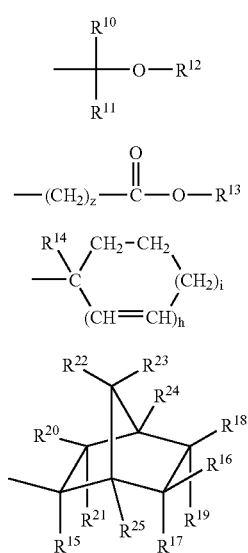

wherein $R^{10}$ and $R^{11}$ each are hydrogen or a straight, branched or cyclic alkyl having 1 to 18 carbon atoms, and $R^{12}$ is a monovalent hydrocarbon group of 1 to 18 carbon atoms which may contain a heteroatom, a pair of $R^{10}$ and $R^{11}$, $R^{10}$ and $R^{12}$, or $R^{11}$ and $R^{12}$ may together form a ring, with the proviso that $R^{10}$, $R^{11}$, and $R^{12}$ each are a straight or branched alkylene of 1 to 18 carbon atoms when they form a ring, $R^{13}$ is a tertiary alkyl group of 4 to 20 carbon atoms, a trialkysilyl group in which each of the alkyls has 1 to 6 carbon atoms, an oxoalkyl group of 4 to 20 carbon atoms, or a group of the formula (4), z is an integer of 0 to 6, $R^{14}$ is a straight, branched or cyclic alkyl group of 1 to 8 carbon atoms or an aryl group of 6 to 20 carbon atoms which may be substituted, h is 0 or 1, i is 0, 1, 2 or 3, satisfying 2h+i=2 or 3, $R^{15}$ is a straight, branched or cyclic alkyl group of 1 to 8 carbon atoms or an aryl group of 6 to 20 carbon atoms which may be substituted, $R^{16}$ to $R^{25}$ are each independently hydrogen or a monovalent hydrocarbon group of 1 to 15 carbon atoms which may contain a heteroatom, any two of $R^{16}$ to $R^{25}$, taken together, may form a ring, each of the ring-forming two of $R^{16}$ to $R^{25}$ is a divalent hydrocarbon group of 1 to 15 carbon atoms which may contain a heteroatom, or two of $R^{16}$ to $R^{25}$ which are attached to adjoining carbon atoms may bond together directly to form a double bond.

12. The resist composition of claim 4 further comprising (D) a basic compound.

13. The resist composition of claim 4 further comprising (E) an organic acid derivative.

14. The resist composition of claim 4 further comprising as an organic solvent a propylene glycol alkyl ether acetate, an alkyl lactate or a mixture thereof.

15. A process for forming a pattern, comprising the steps of:
applying the resist composition of claim 4 onto a substrate to form a coating,
heat treating the coating and exposing the coating to high energy radiation with a wavelength of up to 300 nm or electron beam through a photomask,
optionally heat treating the exposed coating, and developing the coating with a developer.

* * * * *